(12) United States Patent
Lee et al.

(10) Patent No.: US 10,240,035 B2
(45) Date of Patent: Mar. 26, 2019

(54) BLOCK COPOLYMER

(71) Applicant: LG Chem, Ltd., Seoul (KR)

(72) Inventors: Je Gwon Lee, Daejeon (KR); No Jin Park, Daejeon (KR); Jung Keun Kim, Daejeon (KR); Se Jin Ku, Daejeon (KR); Mi Sook Lee, Daejeon (KR); Eun Young Choi, Daejeon (KR); Sung Soo Yoon, Daejeon (KR); Hyung Ju Ryu, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/515,293

(22) PCT Filed: Sep. 30, 2015

(86) PCT No.: PCT/KR2015/010313
§ 371 (c)(1),
(2) Date: Mar. 29, 2017

(87) PCT Pub. No.: WO2016/052994
PCT Pub. Date: Apr. 7, 2016

(65) Prior Publication Data
US 2017/0226261 A1    Aug. 10, 2017

(30) Foreign Application Priority Data

Sep. 30, 2014  (KR) .................. 10-2014-0131964
Jun. 4, 2015   (KR) .................. 10-2015-0079483

(51) Int. Cl.
*C08J 7/12*    (2006.01)
*C08L 53/00*   (2006.01)
(Continued)

(52) U.S. Cl.
CPC ............ *C08L 53/005* (2013.01); *B05D 1/005* (2013.01); *B05D 3/007* (2013.01);
(Continued)

(58) Field of Classification Search
CPC .... E21B 17/01; E21B 2049/085; E21B 34/00; E21B 47/06; E21B 47/065;
(Continued)

(56) References Cited

U.S. PATENT DOCUMENTS 3,976,672 A    8/1976  Strunk et al.
5,115,056 A    5/1992  Mueller et al.
(Continued)

FOREIGN PATENT DOCUMENTS

CN    1333790 A    1/2002
CN    1337974 A    2/2002
(Continued)

OTHER PUBLICATIONS

Chinese Search Report for Application No. 2014800727599 dated Jan. 8, 2018.
(Continued)

*Primary Examiner* — Lan Vinh
(74) *Attorney, Agent, or Firm* — Lerner, David, Littenberg, Krumholz & Mentlik, LLP

(57) ABSTRACT

The present application provides a block copolymer and uses thereof. The block copolymer of the present application exhibits an excellent self-assembling property or phase separation property, can be provided with a variety of required functions without constraint and, especially, etching selectivity can be secured, making the block copolymer effectively applicable to such uses as pattern formation.

21 Claims, 3 Drawing Sheets

(51) Int. Cl.

| | | |
|---|---|---|
| C08F 212/08 | (2006.01) | |
| C08F 216/12 | (2006.01) | |
| C08F 220/10 | (2006.01) | |
| C08F 220/26 | (2006.01) | |
| C08F 220/30 | (2006.01) | |
| C08J 5/18 | (2006.01) | |
| B05D 1/00 | (2006.01) | |
| B05D 3/00 | (2006.01) | |
| C08F 293/00 | (2006.01) | |
| C09D 153/00 | (2006.01) | |
| G03F 7/09 | (2006.01) | |
| G03F 7/16 | (2006.01) | |
| G03F 7/004 | (2006.01) | |
| G03F 7/039 | (2006.01) | |
| G03F 7/20 | (2006.01) | |
| C08F 32/06 | (2006.01) | |
| C08F 299/02 | (2006.01) | |
| C08G 61/08 | (2006.01) | |
| C08F 2/14 | (2006.01) | |
| G03F 7/00 | (2006.01) | |
| G03F 7/30 | (2006.01) | |
| C08L 53/02 | (2006.01) | |
| C08G 61/12 | (2006.01) | |
| B81C 1/00 | (2006.01) | |
| B82Y 40/00 | (2011.01) | |

(52) U.S. Cl.
CPC .......... B81C 1/00428 (2013.01); C08F 2/14 (2013.01); C08F 32/06 (2013.01); C08F 212/08 (2013.01); C08F 216/12 (2013.01); C08F 220/10 (2013.01); C08F 220/26 (2013.01); C08F 220/30 (2013.01); C08F 293/00 (2013.01); C08F 293/005 (2013.01); C08F 299/024 (2013.01); C08G 61/08 (2013.01); C08G 61/128 (2013.01); C08J 5/18 (2013.01); C08J 7/123 (2013.01); C08L 53/00 (2013.01); C08L 53/02 (2013.01); C09D 153/00 (2013.01); G03F 7/0002 (2013.01); G03F 7/0046 (2013.01); G03F 7/091 (2013.01); G03F 7/16 (2013.01); G03F 7/162 (2013.01); G03F 7/2004 (2013.01); G03F 7/30 (2013.01); B81C 2201/0149 (2013.01); B82Y 40/00 (2013.01); C01P 2002/70 (2013.01); C07B 2200/00 (2013.01); C08F 2220/301 (2013.01); C08F 2438/03 (2013.01); C08G 2261/1424 (2013.01); C08G 2261/1426 (2013.01); C08G 2261/332 (2013.01); C08G 2261/3324 (2013.01); C08G 2261/40 (2013.01); C08G 2261/418 (2013.01); C08J 2353/00 (2013.01)

(58) Field of Classification Search
CPC ........ E21B 47/1025; E21B 49/08; G01F 1/68; G01F 1/84; G01M 3/2815; G01N 1/10; G01N 30/02; G01N 33/004; G01N 33/0044; G01N 35/0092; C08F 2220/301; C08F 214/182; C08F 212/08; C08F 216/12; C08F 220/10; C08F 220/26; C08F 220/30; C08F 2438/03; C08F 293/00; C08F 293/005; C08F 299/024; C08F 2/14; C08F 32/06; B05D 1/005; B05D 3/007; B81C 1/00428; B81C 2201/0149; B82Y 40/00; C01P 2002/70; C07B 2200/00; C08G 2261/1424; G03F 7/0002

USPC ...... 252/79.1, 79.2, 500; 430/310, 312, 313, 430/314
See application file for complete search history.

(56) References Cited

U.S. PATENT DOCUMENTS

| | | |
|---|---|---|
| 5,202,402 A | 4/1993 | Funaki et al. |
| 5,234,604 A | 8/1993 | Liao et al. |
| 5,391,626 A | 2/1995 | Machida et al. |
| 5,418,290 A | 5/1995 | Machida et al. |
| 5,554,695 A | 9/1996 | Machida et al. |
| 5,728,431 A | 3/1998 | Bergbreiter et al. |
| 6,025,437 A | 2/2000 | Hirahara et al. |
| 6,314,225 B1 | 11/2001 | Wang |
| 6,531,547 B1 | 3/2003 | Visger et al. |
| 6,546,282 B1 | 4/2003 | Inoue et al. |
| 6,953,649 B2 | 10/2005 | Prat et al. |
| 7,538,159 B2 | 5/2009 | Wang et al. |
| 8,163,189 B2 | 4/2012 | Iyoda et al. |
| 8,211,737 B2 | 7/2012 | Russell et al. |
| 8,791,042 B2 | 7/2014 | Ronan et al. |
| 9,495,991 B2 | 11/2016 | Han et al. |
| 2003/0143343 A1 | 7/2003 | Kawabata et al. |
| 2004/0049836 A1 | 3/2004 | Ashraf et al. |
| 2004/0110856 A1 | 6/2004 | Young et al. |
| 2004/0143032 A1 | 7/2004 | Auschra et al. |
| 2004/0242787 A1 | 12/2004 | Chun et al. |
| 2006/0166033 A1 | 7/2006 | Poetsch et al. |
| 2007/0142559 A1 | 6/2007 | Wang et al. |
| 2007/0166648 A1 | 7/2007 | Ponoth et al. |
| 2007/0219338 A1 | 9/2007 | Takeda et al. |
| 2008/0105854 A1* | 5/2008 | Huh .............. H01B 1/125 252/519.21 |
| 2008/0193658 A1 | 8/2008 | Millward |
| 2008/0213556 A1 | 9/2008 | Cha et al. |
| 2008/0286333 A1 | 11/2008 | Kangas et al. |
| 2008/0311402 A1 | 12/2008 | Jung et al. |
| 2009/0114108 A1 | 5/2009 | Oya et al. |
| 2009/0240001 A1 | 9/2009 | Regner |
| 2009/0253867 A1 | 10/2009 | Takahashi et al. |
| 2009/0306295 A1 | 12/2009 | Mays et al. |
| 2010/0086801 A1 | 4/2010 | Russell et al. |
| 2010/0098876 A1 | 4/2010 | Hanson |
| 2010/0102415 A1 | 4/2010 | Millward et al. |
| 2010/0120985 A1 | 5/2010 | Konishi et al. |
| 2010/0155988 A1 | 6/2010 | Keil et al. |
| 2010/0206057 A1 | 8/2010 | Batchelder et al. |
| 2010/0210742 A1 | 8/2010 | Iyoda et al. |
| 2010/0216312 A1 | 8/2010 | Yamamoto et al. |
| 2010/0266957 A1* | 10/2010 | Harada .............. G03F 7/0046 430/285.1 |
| 2010/0285276 A1 | 11/2010 | Kim et al. |
| 2010/0286351 A1 | 11/2010 | Yoshida et al. |
| 2010/0305230 A1 | 12/2010 | Li et al. |
| 2011/0186544 A1 | 8/2011 | Endou et al. |
| 2011/0253946 A1* | 10/2011 | Huh .............. H01B 1/124 252/501.1 |
| 2011/0294070 A1 | 12/2011 | Hatakeyama et al. |
| 2012/0052446 A1 | 3/2012 | Jaycox et al. |
| 2012/0116024 A1 | 5/2012 | Iyoda et al. |
| 2012/0214094 A1 | 8/2012 | Mikoshiba et al. |
| 2013/0078576 A1 | 3/2013 | Wu et al. |
| 2013/0183828 A1 | 7/2013 | Nakamura et al. |
| 2013/0189504 A1 | 7/2013 | Nealey et al. |
| 2013/0209693 A1 | 8/2013 | Vogel et al. |
| 2013/0209755 A1 | 8/2013 | Hustad et al. |
| 2013/0248488 A1 | 9/2013 | Han et al. |
| 2013/0284698 A1 | 10/2013 | Ogihara |
| 2013/0306594 A1 | 11/2013 | Hustad et al. |
| 2014/0011916 A1 | 1/2014 | Lee et al. |
| 2014/0127456 A1 | 5/2014 | Regner |
| 2014/0141375 A1 | 5/2014 | Cho et al. |
| 2014/0238954 A1 | 8/2014 | Matsumiya et al. |
| 2014/0370442 A1 | 12/2014 | Ober et al. |
| 2015/0064630 A1 | 3/2015 | Wuister et al. |
| 2015/0085042 A1 | 3/2015 | Keoshkerian et al. |

(56) References Cited

U.S. PATENT DOCUMENTS

| | | |
|---|---|---|
| 2015/0197663 A1 | 7/2015 | Mizutani et al. |
| 2015/0228298 A1 | 8/2015 | Han et al. |
| 2016/0204653 A1 | 7/2016 | Lee |
| 2016/0257838 A1 | 9/2016 | Senzaki et al. |
| 2016/0280823 A1 | 9/2016 | Kim et al. |
| 2016/0280831 A1 | 9/2016 | Park et al. |
| 2016/0280832 A1 | 9/2016 | Kim et al. |
| 2016/0280833 A1 | 9/2016 | Lee et al. |
| 2016/0280834 A1 | 9/2016 | Kim et al. |
| 2016/0280835 A1 | 9/2016 | Lee et al. |
| 2016/0304653 A1 | 10/2016 | Kim et al. |
| 2016/0304654 A1 | 10/2016 | Lee et al. |
| 2016/0304655 A1 | 10/2016 | Lee et al. |
| 2016/0311958 A1 | 10/2016 | Kim et al. |
| 2016/0311959 A1 | 10/2016 | Lee et al. |
| 2016/0311960 A1 | 10/2016 | Lee et al. |
| 2016/0333221 A1 | 11/2016 | Mumtaz et al. |
| 2017/0008992 A1 | 1/2017 | Lee et al. |
| 2017/0058071 A1 | 3/2017 | Lee et al. |
| 2017/0210938 A1 | 7/2017 | Ku et al. |
| 2017/0219922 A1 | 8/2017 | Ku et al. |
| 2017/0226235 A1 | 8/2017 | Park et al. |
| 2017/0226258 A1 | 8/2017 | Lee et al. |
| 2017/0226260 A1 | 8/2017 | Lee et al. |
| 2017/0226261 A1 | 8/2017 | Lee et al. |
| 2017/0247492 A1 | 8/2017 | Choi et al. |
| 2017/0306074 A1 | 10/2017 | Lee et al. |
| 2017/0313869 A1 | 11/2017 | Lee et al. |
| 2018/0170023 A1 | 6/2018 | Park et al. |

FOREIGN PATENT DOCUMENTS

| | | |
|---|---|---|
| CN | 101215362 A | 7/2008 |
| CN | 101443371 A | 5/2009 |
| CN | 101492520 A | 7/2009 |
| CN | 101578232 A | 11/2009 |
| CN | 101688047 A | 3/2010 |
| CN | 101799626 A | 8/2010 |
| CN | 101977839 A | 2/2011 |
| CN | 102172491 A | 9/2011 |
| CN | 102439076 A | 5/2012 |
| CN | 102967918 A | 3/2013 |
| CN | 103025827 A | 4/2013 |
| CN | 103180783 A | 6/2013 |
| CN | 103289285 A | 9/2013 |
| CN | 103562245 A | 2/2014 |
| CN | 103797066 A | 5/2014 |
| CN | 105899556 A | 8/2016 |
| CN | 105899557 A | 8/2016 |
| CN | 105899559 A | 8/2016 |
| CN | 105899560 A | 8/2016 |
| CN | 105934454 A | 9/2016 |
| CN | 105934456 A | 9/2016 |
| CN | 105960422 A | 9/2016 |
| CN | 105980342 A | 9/2016 |
| CN | 106459326 A | 2/2017 |
| CN | 107075052 A | 8/2017 |
| EP | 1141056 B1 | 8/2010 |
| EP | 2781550 A1 | 9/2014 |
| EP | 3078654 A1 | 10/2016 |
| EP | 3078691 B1 | 10/2016 |
| EP | 3078692 A1 | 10/2016 |
| EP | 3078694 A1 | 10/2016 |
| EP | 3203497 A1 | 8/2017 |
| EP | 3214102 A1 | 9/2017 |
| EP | 3225641 A1 | 10/2017 |
| GB | 898065 A | 6/1962 |
| JP | 01260360 A | 10/1989 |
| JP | H01260360 A | 10/1989 |
| JP | H5320281 A | 12/1993 |
| JP | H0665333 A | 3/1994 |
| JP | H10237143 A | 9/1998 |
| JP | H10245427 A | 9/1998 |
| JP | H1143523 A | 2/1999 |
| JP | 2000053734 A | 2/2000 |
| JP | 2000281737 A | 10/2000 |
| JP | 2000285751 A | 10/2000 |
| JP | 3121116 B2 | 12/2000 |
| JP | 2001513125 A | 8/2001 |
| JP | 2001294617 A | 10/2001 |
| JP | 2002145973 A | 5/2002 |
| JP | 2003536105 A | 12/2003 |
| JP | 2004026688 A | 1/2004 |
| JP | 2004323773 A | 11/2004 |
| JP | 2005015508 A | 1/2005 |
| JP | 2005097442 A | 4/2005 |
| JP | 2005148205 A | 6/2005 |
| JP | 2005530030 A | 10/2005 |
| JP | 2005531618 A | 10/2005 |
| JP | 2007070453 A | 3/2007 |
| JP | 2007077292 A | 3/2007 |
| JP | 2007246600 A | 9/2007 |
| JP | 200855579 A | 3/2008 |
| JP | 2009057519 A | 3/2009 |
| JP | 200986354 A | 4/2009 |
| JP | 2009203439 A | 9/2009 |
| JP | 2010507803 A | 3/2010 |
| JP | 2010115832 A | 5/2010 |
| JP | 2010116466 A | 5/2010 |
| JP | 2010145158 A | 7/2010 |
| JP | 2010202723 A | 9/2010 |
| JP | 2010275349 A | 12/2010 |
| JP | 4625901 B2 | 2/2011 |
| JP | 2012001787 A | 1/2012 |
| JP | 2012012577 A | 1/2012 |
| JP | 2012093699 A | 5/2012 |
| JP | 2012174984 A | 9/2012 |
| JP | 201368882 A | 4/2013 |
| JP | 2013512323 A | 4/2013 |
| JP | 2013514449 A | 4/2013 |
| JP | 2013121430 A | 6/2013 |
| JP | 2013219334 A | 10/2013 |
| JP | 2013232501 A | 11/2013 |
| JP | 201412807 A | 1/2014 |
| JP | 2014070154 A | 4/2014 |
| JP | 2014102503 A | 6/2014 |
| JP | 2014162504 A | 9/2014 |
| JP | 2015000896 A | 1/2015 |
| JP | 2016539239 A | 12/2016 |
| JP | 2016540863 A | 12/2016 |
| JP | 2017502116 A | 1/2017 |
| JP | 2017505356 A | 2/2017 |
| JP | 2017530236 A | 10/2017 |
| JP | 2017530238 A | 10/2017 |
| JP | 2017533302 A | 11/2017 |
| KR | 20010101356 | 11/2001 |
| KR | 100622353 B1 | 9/2006 |
| KR | 20090015742 A | 2/2009 |
| KR | 100935863 B1 | 1/2010 |
| KR | 20100033962 A | 3/2010 |
| KR | 20100070380 A | 6/2010 |
| KR | 20100123920 A | 11/2010 |
| KR | 20110018678 A | 2/2011 |
| KR | 20110086834 A | 8/2011 |
| KR | 20110097707 A | 8/2011 |
| KR | 20110102998 A | 9/2011 |
| KR | 20110112501 A | 10/2011 |
| KR | 101102680 B1 | 1/2012 |
| KR | 20120119998 A | 11/2012 |
| KR | 20130094264 A | 8/2013 |
| KR | 20130113596 A | 10/2013 |
| KR | 20130128346 A | 11/2013 |
| KR | 20140063790 A | 5/2014 |
| KR | 20150066488 A | 6/2015 |
| KR | 20150067065 A | 6/2015 |
| KR | 20150067069 A | 6/2015 |
| KR | 20150067070 A | 6/2015 |
| KR | 20160038705 A | 4/2016 |
| TW | 201323461 A | 6/2013 |
| TW | 201428046 A | 7/2014 |
| TW | 201536823 A | 10/2015 |
| TW | 201538548 A | 10/2015 |
| WO | 9837136 A1 | 8/1998 |
| WO | 2007055371 A1 | 5/2007 |

(56) References Cited

FOREIGN PATENT DOCUMENTS

| WO | 2012144735 A2 | 10/2012 |
|---|---|---|
| WO | 2013069544 A1 | 5/2013 |
| WO | 2013120051 A1 | 8/2013 |
| WO | 2013158527 A1 | 10/2013 |
| WO | 2014050905 A1 | 4/2014 |
| WO | 2014090178 A1 | 6/2014 |
| WO | 2014124795 A1 | 8/2014 |
| WO | 2015084121 A1 | 6/2015 |
| WO | 2015084122 A1 | 6/2015 |
| WO | 2015084123 A1 | 6/2015 |
| WO | 2015084124 A1 | 6/2015 |
| WO | 2015084125 A1 | 6/2015 |
| WO | 2015084126 A1 | 6/2015 |
| WO | 2015084127 A1 | 6/2015 |
| WO | 2015087005 A1 | 6/2015 |
| WO | 2016052994 A1 | 4/2016 |
| WO | 2016052999 A1 | 4/2016 |
| WO | 2016053005 A1 | 4/2016 |
| WO | 2016053007 A1 | 4/2016 |
| WO | 2016053011 A1 | 4/2016 |

OTHER PUBLICATIONS

Chinese Search Report for Application No. 2014800741401 dated Mar. 9, 2018.
Chinese Search Report for Application No. 201480074156.2 dated Apr. 3, 2018.
Supplementary European Search Report for EP15847157 dated Mar. 21, 2018.
CN Search Report for Application No. 201480071920.0 dated Aug. 2, 2017.
CN Search Report for Application No. CN201480072884.X dated Aug. 3, 2017.
CN Search Report for Application No. CN2014800740447 dated Aug. 1, 2017.
Extended European Search Report for Application No. EP14867273 dated Aug. 10, 2017.
Mariana Beija et al: "Fluorescence Anisotropy of Hydrophobic Probes in poly(N-decylacrylamide) block-poly( N,N-diethylacrylamide) Block Copolymer Aqeos Solutions: Evidence of Premicellar Aggregates" Journal of Physical Chemistry Part B: Condensed Matter, Materials, Surfaces, Interfaces & Bi0physical, vol. 114, No. 31, Aug. 12, 2010 (Aug. 12, 2010), 9977-9986, XP055394763, US ISSN: 1520-6106, D0I: 10.1021/jp101613y * abstract * * Scheme 1, PDcA11-block-PDEA295; p. 9978 *.
Database CA [Online] Chemical Abstracts Service Ohi0 US; Zou, Yue: "Fluorosurfactant capable of preventing unevenness in photoresist coating and its preparation by anionic polymerization", XP002771143 retrieved from STN Database accession No. 2011:1148166 * abstract * & CN 102 172 491 A (Jiangsu Johnny Material Technology Co Ltd) Sep. 7, 011 (Sep. 7, 2011) Columbus, No. 2011:1148166.
European Search Report for Application No. EP14867501 dated Jul. 14, 2017.
Kago K et al: "X-ray reflectivity of polymer assembly at air-water interface" Supramolecular Science Butterworth-Heinemann Oxford GB vol. 5 No. 3-4, Jul. 1, 1998 (Jul. 1, 1998)pp. 349-355 XP027388373 ISSN: 0968-5677 [retrieved on Jul. 1, 1998] * abstract *.
Lutz Funk et al: "Novel Amphiphilic Styrene-Based Block Copolymers for Induced Surface Reconstruction". Macromolecular Chemistry and Physics., vol. 209, No. 1, Jan. 4, 2008 (Jan. 4, 2008), XP055382259 DE ISSN: 1022-1352 D0I: 10.1002/macp. 200700312 * scheme 1, monomers M1, M4 table 2*.
Mori H et al: "Synthesis and Surface Characterization of Hydrophilic-Hydrophobic Block Copolymers Containing Poly(2, 3-Dihydroxypropyl Methacrylate)"Macromolecules American Chemical Society US vol. 27 No. 15 Jul. 18, 1994 (Jul. 18, 1994) pp. 4093-4100 XP000456650 ISSN: 0024-9297 D01: 10.102/1MA00093A010 * abstract *.

Anonymous., "Solid surface energy data (SFE) for common polymers", surface-tension.de, Feb. 2017, Retreived from the Internet: URL:http://www.surface-tension.de/solid-surface-energy.htm, XP002775246.
Cummins et al., "Solvothermal Vapor Annealing of Lamellar Poly-(styrene)-block-poly(D,L-lactide) Block Copolymer Thin Films for Directed Self-Assembly Application", ACS Applied Materials & Interfaces, Mar. 2016, vol. 8, No. 12, pp. 8295-8304, XP055419698.
Extended European Search Report for Application No. EP14867808.9 dated Nov. 10, 2017.
Extended European Search Report for Application No. EP14868022.6 dated Nov. 6, 2017.
Extended European Search Report for Application No. EP14868320.4 dated Nov. 20, 2017.
Extended European Search Report for Application No. EP14868480.6 dated Nov. 2, 2017.
Hvilsted et al., "Novel Fluorinated Polymer Materials Based on 2,3,5,6-Tetrafluoro-4-methoxyystyrene" In: "Advances in Controlled/Living Radical Polymerization", American Chemical Society, Jun. 26, 2003, vol. 854, pp. 236-249, XP055421064.
Mahajan et al., "Synthesis and Characterization of Amphiphilic Poly(ethylene oxide)-block-poly(hexylmethacrylate Copolymers", Macromolecular Chemistry and Physics, Wiley-Vch Verlag, Weinheim, DE, Jan. 2003, vol. 204, pp. 1047-1055, XP003030406.
Pochan et al., "Morphologies of microphase-seperated conformationally asymmetric diblock copolymers", Journal of Polymer Science Part B: Polymer Physics, Nov. 2017, vol. 35, No. 16, pp. 2629-2643, XP055417266.
Zhuang et al., "Synthesis of A-B type block copolymers using 1-phenylethyl dithiobenzoate as Reversible Addition-Fragmentation Chain Transfer agent", Database CA [online], Chemical Abstracts Service, Columbus, OH, XP002775247.
U.S. Appl. No. 15/102,139, filed Jun. 6, 2016.
U.S. Appl. No. 15/102,149, filed Jun. 6, 2016.
U.S. Appl. No. 15/102,156, filed Jun. 6, 2016.
U.S. Appl. No. 15/173,670, filed Jun. 5, 2016.
U.S. Appl. No. 15/173,671, filed Jun. 5, 2016.
U.S. Appl. No. 15/173,673, filed Jun. 5, 2016.
U.S. Appl. No. 15/173,674, filed Jun. 5, 2016.
U.S. Appl. No. 15/173,676, filed Jun. 5, 2016.
U.S. Appl. No. 15/514,929, filed Mar. 28, 2017.
U.S. Appl. No. 15/514,939, filed Mar. 28, 2017.
U.S. Appl. No. 15/514,959, filed Mar. 28, 2017.
U.S. Appl. No. 15/514,967, filed Mar. 28, 2017.
U.S. Appl. No. 15/515,290, filed Mar. 29, 2017.
U.S. Appl. No. 15/515,293, filed Mar. 29, 2017.
U.S. Appl. No. 15/515,432, filed Mar. 29, 2017.
U.S. Appl. No. 15/515,812, filed Mar. 30, 2017.
U.S. Appl. No. 15/515,818, filed Mar. 30, 2017.
U.S. Appl. No. 15/515,821, filed Mar. 30, 2017.
Riedel et al., Synthesis, post-modification and self-assembled thin films of pentafluorostyrene containing block copolymers, European Polymer Journal 47 (2011) 675-684.
Yoshida, E. et al. Polymer Journal vol. 31 (5) pp. 429-434 (1999).
Chakrabarty, et al, "Tailor-Made Polyfluoroacrylate and its Block Copolymer by RAFT Polymerization in Miniemulsion; Improved Hydrophobicity in the Core-Shell Block Copolymer", Journal of Colloid and Interface Science, vol. 408, Oct. 2013, pp. 66-74.
Gregory, et al., "Complex Polymer Architectures via RAFT Polymerization: From Fundamental Process to Extending the Scope Using Click Chemistry and Nature's Building Blocks", Progress in Polymer Science, vol. 37, No. 1, Jan. 2012, pp. 38-105.
EESR for EP Application No. 15847536.8 dated Aug. 23, 2018, 6 pages.
Chinese Search Report for Application No. 201480072759.9 dated Jan. 24, 2018.
Palacios et al., Constructing Robust and Functional Micropatterns on Polystyrene Surfaces by Using Deep UV Irradiation, American Chemical Society, Langmuir, 29(8) pp. 2756-2763, Feb. 2013.
Chinese Search Report for Application No. CN201580059758.5 dated Sep. 5, 2018.
Chinese Search Report for Application No. CN201580060097.8 dated Sep. 19, 2018.

(56) References Cited

OTHER PUBLICATIONS

Beng H. Tan et al., "Synthesis and Self-Assembly of pH-Responsive Amphiphilic Poly (dimethylaminoethylmethacrylate)-block-Poly(pentafluorostyrene) Block Copolymer in Aqueous Solution", Macromolecular Rapid Communications, Jun. 17, 2009, vol. 30 (12), pp. 1002-1008.

C.M. Bates et al., "Polymeric Cross-Linked Surface Treatments for Controlling Block Copolymer Orientation in Thin Films", Langmuir Article, American Chemical Society, Jan. 7, 2011, vol. 27, No. 5, pp. 1-7.

Chinese Search Report for CN Application No. 201480071920.0, dated May 4, 2018, completed Apr. 25, 2018.

Chinese Search Report for CN Application No. 201480072800.2, dated Apr. 10, 2018, completed Mar. 27, 2018.

Chinese Search Report for CN Application No. 2014800740447 dated Jun. 7, 2018, completed May 30, 2018.

Chinese Search Report for CN Application No. 201480074045.1, dated Apr. 11, 2018, completed Mar. 29, 2018.

Extended European Seach Report including Written Opinion for EP Application No. 15847574.9, dated May 3, 2018.

Extended European Search Report including Written Opinion for Application No. EP15845665.7 dated Jun. 27, 2018.

Extended European Search Report including Written Opinion for EP Application No. 15845928.9, dated May 2, 2018.

Extended European Search Report including Written Opinion for EP Application No. 15847598.8, dated May 11, 2018.

Extended European Search Report including Written Opinion for EP15845720.0 dated May 4, 2018.

Extended European Search Report with Written Opinion for EP158468322 dated May 3, 2018.

Frank S. Bates et al., "Block Copolymer Thermodyanmics: Theory and Experiment", Annu. Rev. Phys. Chem., Oct. 1990, vol. 41 (1), pp. 525-557.

Funk, L. et al., "Novel Amphiphilic Styrene-Based Block Copolymers for Induced Surface Reconstruction," Macromolecular Chemistry and Physics, vol. 209, No. 1, Jan. 4, 2008, pp. 52-63, XP055382259.

G.R. Strobl, "The Physics of Polymers: Concepts for Understanding Their Structures and Behavior", Springer (Abstract Only).

Haeng-Dong Koh et al., "Location-controlled parallel and vertical orientation by dewetting-induced block copolymer directed self-assembly," Journal of Materials Chemistry C: Materials for Optical and Electronic Devices, vol. 1, No. 25, Jan. 1, 2013, pp. 4020-4024 XP055469744.

Katja Nilles et al., "RAFT Polymerization of Activated 4-Vinylbenzoates"., Journal of Polymer Science: Part A: Polymer Chemistry, Jan. 1, 2009, vol. 47, pp. 1696-1705.

Ma J et al., "Synthesis and Solution-State Assembly or Buld State Thiol-ene Crosslinking of Pyrrolidinone- and Alkene-Functionalized Amphiphilic Block Fluoropolymers: From Functional Nanaparticles to Anti-Fouling Coatings", Australian Journal of Chemistry: An International Journal of Chemical Sci, Jan. 1, 2010, pp. 1159-1163, vol. 63, No. 8, C S I R O Publishing, Australia.

Mori H. et al., "Synthesis and Surface Characterization of Hydrophilic-Hydrophobic Block Copolymers Containing Poly(2,3-dihydroxypropyl methacrylate)," Macromolecules, American Chemical Society, US, vol. 27, No. 15, Jul. 18, 1994, pp. 4093-9297; XP000456650, DOI: 102021/MA00093A010.

P. Chavda et al., "Synthesis of stimuli responsive PEG47-b-PAA126-b-PSt32 triblock copolymer and its self-assembly in aqueous solutions", European Polymer Journal, Sep. 2012, vol. 49, pp. 209-216.

Sachin Borkar et al, "New Highly Fluorinated Styrene-Based Materials with Low Surface Energy Prepared by ATRP", Macromolecules, Jan. 2004, vol. 37, pp. 788-794.

Segalman R.A. et al., "Graphoepitaxy of Spherical Domain Block Copolymer Films," Advanced Materials, Wiley—VCH Verlag GmbH & Co. KGAA, DE, vol. 13, No. 15, Aug. 3, 2001, pp. 1152-1155; XP001129643.

Truelsen et al., "Synthesis by ATRP of triblock copolymers with densely grafted styrenic end blocks from a Dolyisobutylene macroinitiator", Marcomol. Rapid. Commun., Jul. 2, 1999, vol. 21, No. 2, pp. 1-5.

Akiba, Isamu, et al., "Self-Assembly of Amphiphilic Block Copolymers Containing Poly(n-octadecyl acrylate) Block in Aqueous Solution." IOP Conference Series: Materials Science and Engineering, 2010, vol. 14, No. 1, pp. 1-8.

Hua et al. Temperature-induced phase-transitions of methoxyoligo(oxyethylene) styrene-based block copolymers in aqueous solution, Soft Matter, 2013, 9, 8897.

International Search Report from PCT/KR2014/012023, dated Mar. 10, 2015.

International Search Report from PCT/KR2014/012024, dated Mar. 17, 2015.

International Search Report from PCT/KR2014/012025, dated Mar. 17, 2015.

International Search Report from PCT/KR20141012026, dated Mar. 17, 2015.

International Search Report from PCT/KR2014/012027, dated Mar. 17, 2015.

International Search Report from PCT/KR2014/012028, dated Mar. 17, 2015.

International Search Report from PCT/KR2014/012029, dated Mar. 17, 2015.

International Search Report from PCT/KR2014/012030, dated Mar. 17, 2015.

International Search Report from PCT/KR2014/012031, dated Feb. 12, 2015.

International Search Report from PCT/KR2014/012032, dated Feb. 12, 2015.

International Search Report from PCT/KR2014/012033, dated Feb. 12, 2015.

International Search Report from PCT/KR2014/012034, dated Feb. 12, 2015.

International Search Report from PCT/KR2014/012035, dated Feb. 12, 2015.

International Search Report from PCT/KR2014/012036, dated Mar. 17, 2015.

International Search Report from PCT/KR2015/010313, dated Nov. 23, 2015.

International Search Report from PCT/KR2015/010320, dated Jan. 13, 2016.

International Search Report from PCT/KR2015/010322, dated Jan. 13, 2016.

International Search Report from PCT/KR2015/010323, dated Jan. 13, 2016.

International Search Report from PCT/KR2015/010327, dated Jan. 12, 2016.

International Search Report from PCT/KR2015/010330 dated Jan. 11, 2016.

International Search Report from PCT/KR2015/010332 dated Jan. 13, 2016.

International Search Report from PCT/KR2015/010334, dated Jan. 13, 2016.

International Search Report from PCT/KR2015/010335 dated Jan. 13, 2016.

International Search Report from PCT/KR2015/010338 dated Jan. 14, 2016.

IPO Search Report from Taiwan Application No. 103142745, dated Dec. 14, 2015.

IPO Search Report from Taiwan Application No. 103142777, dated Dec. 15, 2015.

IPO Search Report from Taiwan Application No. 103142780, dated Dec. 15, 2015.

IPO Search Report from Taiwan Application No. 103142784, dated Jan. 27, 2016.

IPO Search Report from Taiwan Application No. 103142786, dated Jan. 11, 2016.

IPO Search Report from Taiwan Application No. 103142790, dated Dec. 15, 2015.

IPO Search Report from Taiwan Application No. 103142794, dated Dec. 15, 2015.

(56) References Cited

OTHER PUBLICATIONS

IPO Search Report from Taiwan Application No. 103142798, dated Dec. 16, 2015.
IPO Search Report from Taiwan Application No. 103142805, dated Dec. 11, 2015.
IPO Search Report from Taiwan Application No. 103142955, dated Jan. 15, 2016.
IPO Search Report from Taiwan Application No. 103142956 dated Jan. 20, 2016.
IPO Search Report from Taiwan Application No. 103142963, dated Dec. 10, 2015.
IPO Search Report from Taiwan Application No. 104132186, dated Aug. 18, 2016.
IPO Search Report from Tawain Application No. 103142782, dated Dec. 11, 2015.
Khazimullis et al. "Gel formation in a mixture of a block copolymer and a nematic liquid crystal", Physical Review E 34, 021710 (2011).
Park et al., "Block Copolymer Lithography: Periodic Arrays of ~10 11 Holes in 1 Square Centimeter", Science 276, p. 1401-1404, May 30, 1997.
Tenneti et al. "Competition between liquid crystallinity and block copolymer self-assembly in core-shell rod-coil block copolymers", Soft Matter, 2008, 4, 458-461 (2008).
Tenneti et al. Hierarchical Nanostructures of Mesogen Jacketed Bent-Core Liquid Crystalline Block Copolymers, Proceedings Published 2007 by the American Chemical Society.
U.S. Appl. No. 15/101,794, filed Jun. 3, 2016.
U.S. Appl. No. 15/101,812, filed Jun. 3, 2016.
U.S. Appl. No. 15/101,827, filed Jun. 3, 2016.
U.S. Appl. No. 15/101,915, filed Jun. 5, 2016.
U.S. Appl. No. 15/102,089, filed Jun. 6, 2016.
U.S. Appl. No. 15/102,112, filed Jun. 6, 2016.

\* cited by examiner

BLOCK COPOLYMER

CROSS-REFERENCE TO RELATED APPLICATIONS

The present application is a national phase entry under 35 U.S.C. § 371 of International Application No. PCT/KR2015/010313, filed Sep. 30, 2015, published in Korean, which claims priority to and the benefit of Korean Patent Application No. 2014-0131964, filed on Sep. 30, 2014, and No. 2015-0079483, filed on Jun. 4, 2015, the disclosures of which are incorporated herein by reference in their entirety.

FIELD

The present application relates to a block copolymer and uses thereof.

BACKGROUND

The block copolymer has a molecular structure in which polymer blocks, each with a distinct chemical structure, are connected to one another by covalent bonds. The block copolymer can be constructed in a regularly arranged structure—such as a sphere, a cylinder, and a lamella—through phase separation. The structure that is formed as the result of the self-assembly phenomenon of a block copolymer has a domain whose size can be adjusted over a wide range, and it can be constructed in various forms which can be applied to the production of a variety of next-generation nanodevices, magnetic storage media, and patterns (by lithography or the like): to be specific, the production of high-density magnetic recording media, nanowires, quantum dots, metal dots or the like.

Material properties of a block copolymer required for use in the above production of patterns include an etching selectivity plus a self-assembling property. That is, the fabrication of a mask for the production of a pattern may require a process of selectively removing any one block among the blocks—that are chemically different from one another—of a self-assembled block copolymer; in the case that the etching selectivity among the blocks is not secured during the above process, it is difficult for the block copolymer to be used in the production of a pattern.

DESCRIPTION

Object

The present application provides block copolymers and uses thereof.

Solution

Unless specifically indicated otherwise, the term "an alkyl group" in the present specification may refer to an alkyl group with 1 to 20 carbons, 1 to 16 carbons, 1 to 12 carbons, 1 to 8 carbons or 1 to 4 carbons. The above alkyl group may be a linear-type, a branched-type or a ring-type, and it may be optionally substituted in part by one or more substituents.

Unless specifically indicated otherwise, the term "an alkoxy group" in the present specification may refer to an alkoxy group with 1 to 20 carbons, 1 to 16 carbons, 1 to 12 carbons, 1 to 8 carbons or 1 to 4 carbons. The above alkoxy group may be a linear-type, a branched-type or a ring-type, and it may be optionally substituted in part by one or more substituents.

Unless specifically indicated otherwise, the term "an alkenyl group" or "an alkynyl group" in the present specification may refer to an alkenyl group or alkynyl group with 2 to 20 carbons, 2 to 16 carbons, 2 to 12 carbons, 2 to 8 carbons or 2 to 4 carbons. The above alkenyl group or alkynyl group may be a linear-type, a branched-type or a ring-type, and it may be optionally substituted in part by one or more substituents.

Unless specifically indicated otherwise, the term "an alkylene group" in the present specification may refer to an alkylene group with 1 to 20 carbons, 1 to 16 carbons, 1 to 12 carbons, 1 to 8 carbons or 1 to 4 carbons. The above alkylene group may be a linear-type, a branched-type or a ring-type, and it may be optionally substituted in part by one or more substituents.

Unless specifically indicated otherwise, the terms "an alkenylene group" or "an alkynylene group" in the present specification may refer to an alkenylene group or alkynylene group with 2 to 20 carbons, 2 to 16 carbons, 2 to 12 carbons, 2 to 8 carbons or 2 to 4 carbons. The above alkenylene group or alkynylene group may be a linear-type, a branched-type or a ring-type, and it may be optionally substituted in part by one or more substituents.

Unless specifically indicated otherwise, the term "an aryl group" or "an arylene group" in the present specification may refer to a monovalent or divalent residue that is derived from a compound that has a benzene ring structure or a structure in which two or more benzene rings are connected to one another (either by sharing one or two carbon atoms or by any linker) or from a derivative of the above compound. Unless specifically indicated otherwise, the above aryl group or arylene group may refer to an aryl group with, for example, 6 to 30 carbons, 6 to 25 carbons, 6 to 21 carbons, 6 to 18 carbons, or 6 to 13 carbons.

In the present application, the term "an aromatic structure" may refer to the above aryl group or arylene group.

In the present specification, the term "an alicyclic ring structure" refers to, unless specifically indicated otherwise, a ring-type hydrocarbon atom structure other than an aromatic ring structure. Unless specifically indicated otherwise, the above alicyclic ring structure may refer to an alicyclic ring structure with, for example, 3 to 30 carbons, 3 to 25 carbons, 3 to 21 carbons, 3 to 18 carbons, or 3 to 13 carbons.

In the present application, the term "a single bond" may refer to the case in which a particular atom is not present in the corresponding area. For example, when B denotes a single bond in the structure that is represented by A-B-C, it may be assumed that there is no particular atom present in the region that is marked as B, resulting in a direct connection between A and C to form the structure that is represented by A-C.

In the present application, examples of the substituent that may be optionally substituted for a part or parts of an alkyl group, an alkenyl group, an alkynyl group, an alkylene group, an alkenylene group, an alkynylene group, an alkoxy group, an aryl group, an arylene group, a chain, an aromatic structure or the like may include, but are not limited to, a hydroxyl group, a halogen atom, a carboxyl group, a glycidyl group, an acryloyl group, a methacryloyl group, an acryloyloxy group, a methacryloyloxy group, a thiol group, an alkyl group, an alkenyl group, an alkynyl group, an alkylene group, an alkenylene group, an alkynylene group, an alkoxy group, an aryl group and the like.

The block copolymer of the present application may contain a block (which may be referred to as the block 1 hereinafter) that contains a structural unit represented by the following Structural Formula 1. The block 1 may either consist only of the structural unit represented by the following Structural Formula 1 or contain another structural unit in addition to the above structural unit represented by Structural Formula 1.

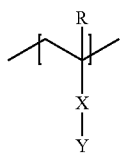

[Structural Formula 1]

In Structural Formula 1, R represents a hydrogen atom or an alkyl group; X represents a single bond, an oxygen atom, a sulfur atom, —S(=O)$_2$—, a carbonyl group, an alkylene group, an alkenylene group, an alkynylene group, —C(=O)—X$_1$— or —X$_1$—C(=O)—, where the X$_1$ represents an oxygen atom, a sulfur atom, —S(=O)$_2$—, an alkylene group, an alkenylene group or an alkynylene group; and Y represents a monovalent substituent that includes a ring structure to which a chain containing 8 or more chain-forming atoms is connected.

In another embodiment, the X of Structural Formula 1 may represent a single bond, an oxygen atom, a carbonyl group, —C(=O)—O—, —O—C(=O)— or —C(=O)—O—, although it is not limited thereto.

The monovalent substituent represented by the Y of Structural Formula 1 includes a chain structure constructed by at least 8 chain-forming atoms.

In the present application, the term "a chain-forming atom" refers to an atom that forms a linear structure of a predetermined chain. The chain may be a linear-type or a branched-type, but the number of chain-forming atoms is counted only by the number of atoms that form the longest linear chain, and the other atoms that are bonded to the above chain-forming atoms (e.g. when the chain-forming atom is a carbon atom, the hydrogen atom or the like that is bonded to the carbon atom) are not taken into account. In the case of a branched-type chain, the number of chain-forming atoms may be counted by the number of chain-forming atoms that form the longest chain. For example, when the chain is an n-pentyl group, all of the chain-forming atoms are carbon and the number of the chain-forming atoms is five, and when the above chain is a 2-methylpentyl group, all of the chain-forming atoms are carbon and the number of the chain-forming atoms is 5. Examples of a chain-forming atom may include carbon, oxygen, sulfur, and nitrogen; a suitable chain-forming atom may be any one of carbon, oxygen and nitrogen, or any one of carbon and oxygen. The number of chain-forming atoms in a chain may be 8 or more, 9 or more, 10 or more, 11 or more, or 12 or more. The number of chain-forming atoms in a chain may also be 30 or less, 25 or less, 20 or less, or 16 or less.

The structural unit represented by Structural Formula 1 can provide an excellent self-assembling property to the above block copolymer to which it belongs.

In one embodiment, the aforementioned chain may be a linear hydrocarbon chain such as a linear alkyl group. In such a case, the alkyl group may be an alkyl group with 8 or more carbons, 8 to 30 carbons, 8 to 25 carbons, 8 to 20 carbons, or 8 to 16 carbons. One or more carbon atoms in the above alkyl group may each be substituted optionally by an oxygen atom, and at least one hydrogen atom in the alkyl group may each be substituted optionally by another substituent.

In Structural Formula 1, the Y may include a ring structure, and the above chain may be connected to the ring structure. Such a ring structure may contribute to the further improvement of a self-assembling property and the like of the block copolymer that is made of the monomer to which it belongs. The ring structure may be an aromatic structure or an alicyclic structure.

The above chain may be connected to the above ring structure either directly or by a linker. Examples of the linker may include an oxygen atom, a sulfur atom, —NR$_1$—, —S(=O)$_2$—, a carbonyl group, an alkylene group, an alkenylene group, an alkynylene group, —C(=O)—X$_1$— and —X$_1$—C(=O)—, where the R$_1$ may represent a hydrogen atom, an alkyl group, an alkenyl group, an alkynyl group, an alkoxy group or an aryl group, and the X$_1$ may represent a single bond, an oxygen atom, a sulfur atom, —NR$_2$—, —S(=O)$_2$—, an alkylene group, an alkenylene group or an alkynylene group, where the R$_2$ may represent a hydrogen atom, an alkyl group, an alkenyl group, an alkynyl group, an alkoxy group, or an aryl group. Examples of a suitable linker may include an oxygen atom and a nitrogen atom. The above chain may be connected to an aromatic structure, for example, by an oxygen atom or a nitrogen atom. In this case, the above linker may be an oxygen atom or —NR$_1$— (where R$_1$ represents a hydrogen atom, an alkyl group, an alkenyl group, an alkynyl group, an alkoxy group, or an aryl group).

In one embodiment, the Y of Structural Formula 1 may be represented by the following Structural Formula 2.

—P-Q-Z  [Structural Formula 2]

In Structural Formula 2, P represents an arylene group; Q represents a single bond, an oxygen atom or —NR$_3$—, where the R$_3$ represents a hydrogen atom, an alkyl group, an alkenyl group, an alkynyl group, an alkoxy group or an aryl group; and Z represents the aforementioned chain that contains 8 or more chain-forming atoms. When the Y of Structural Formula 1 is the substituent represented by Structural Formula 2, the P of Structural Formula 2 may be connected directly to the X of Structural Formula 1.

A suitable embodiment of the P of Structural Formula 2 may include, but is not limited to, an arylene group with 6 to 12 carbons, for example, a phenylene group.

Suitable embodiments of the Q of Structural Formula 2 may include an oxygen atom and —NR$_1$— (where the R$_1$ represents a hydrogen atom, an alkyl group, an alkenyl group, an alkynyl group, an alkoxy group, or an aryl group).

A suitable embodiment of the structural unit of Structural Formula 1 may include a structural unit of Structural Formula 1, where the R represents a hydrogen atom or an alkyl group (e.g. an alkyl group with 1 to 4 carbons), the X represents —C(=O)—O—, and the Y is represented by Structural Formula 2, where the P represents a phenylene or an arylene group with 6 to 12 carbons, the Q represents an oxygen atom, and the Z represents the aforementioned chain containing 8 or more chain-forming atoms.

Therefore, a suitable illustrative structural unit of Structural Formula 1 may include the structural unit represented by the following Structural Formula 3.

[Structural Formula 3]

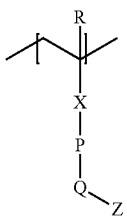

In Structural Formula 3, R represents a hydrogen atom or an alkyl group with 1 to 4 carbon atoms, X represents —C(=O)—O—, P represents an arylene group with 6 to 12 carbons, Q represents an oxygen atom, and Z represents the aforementioned chain containing 8 or more chain-forming atoms.

In another embodiment, the structural unit (represented by Structural Formula 1) of the block 1 may also be represented by the following Structural Formula 4.

[Structural Formula 4]

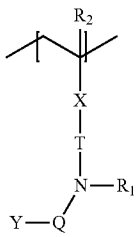

In Structural Formula 4, each of $R_1$ and $R_2$ independently represents a hydrogen atom or an alkyl group with 1 to 4 carbons; X represents a single bond, an oxygen atom, a sulfur atom, —S(=O)$_2$—, a carbonyl group, an alkylene group, an alkenylene group, an alkynylene group, —C(=O)—X$_1$— or —X$_1$—C(=O)—, where the $X_1$ represents a single bond, an oxygen atom, a sulfur atom, —S(=O)$_2$—, an alkylene group, an alkenylene group or an alkynylene group; T represents a single bond or an arylene group; Q represents a single bond or a carbonyl group; and Y represents a chain containing 8 or more chain-forming atoms.

In Structural Formula 4, the X may represent a single bond, an oxygen atom, a carbonyl group, —C(=O)—O—, or —O—C(=O)—.

Specific examples of the chain of the Y of Structural Formula 4 may be similar to what has been described of Structural Formula 1.

In another embodiment, an electronegativity of 3 or greater may be observed in at least one chain-forming atom of a chain (with 8 or more chain-forming atoms) that is contained in any one of the structural units (represented by Structural Formulae 1, 3 and 4) of the block 1. In another embodiment, the electronegativity of the above atom(s) may be 3.7 or less. Examples of the above atom(s) whose electronegativity is 3 or greater may include, but are not limited to, a nitrogen atom and an oxygen atom.

The block 2 that is contained in a block copolymer together with the block 1, which contains the above-described structural units, may contain at least the structural unit that is represented by the following Structural Formula 5.

[Structural Formula 5]

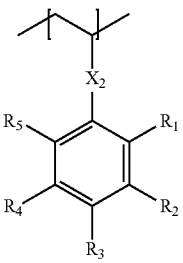

In Structural Formula 5, $X_2$ represents a single bond, an oxygen atom, a sulfur atom, —S(=O)$_2$—, an alkylene group, an alkenylene group, an alkynylene group, —C(=O)—X$_2$— or —X$_2$—C(=O)—, where the $X_2$ represents a single bond, an oxygen atom, a sulfur atom, —S(=O)$_2$—, an alkylene group, an alkenylene group or an alkynylene group; and each of $R_1$ to $R_5$ independently represents a hydrogen atom, an alkyl group, a haloalkyl group, an halogen atom or a photo crosslinkable functional group, where the number of a photo crosslinkable functional group(s) contained in the positions marked as $R_1$ to $R_5$ is 1 or more.

The block 2 may consist only of the structural unit represented by Structural Formula 5 or contain one or more additional structural units that will be described below in the present specification. When the block 2 contains one or more additional structural units in addition to the structural unit that is represented by Structural Formula 5, each of the structural units may form a separate subblock, or be randomly positioned, in the block 2.

As described above, the structural unit that is represented by Structural Formula 5 contains at least one photo crosslinkable functional group. The block copolymer can be crosslinked by such a photo crosslinkable functional group before or after the formation of a self-assembled structure. When the crosslinking reaction is induced only in the block 2, the etching selectivity between the block 1 and the block 2 can be improved.

As a photo crosslinkable functional group included in the unit of Structural Formula 5, a functional group (hereinafter, referred to as a photo-radical generating group) that can be crosslinked with generating radicals when being irradiated with light or a functional group that does not generate radicals however can be crosslinked in the presence of radicals can be illustrated. In a case of the latter group, the block copolymer may be used in the process along with an appropriate radical initiator. As a photo crosslinkable functional group, benzoylphenoxy group, alkenyloxycarbonyl group, (meth)acryloyl group or alkenyloxyalkyl group may be illustrated, but is not limited thereto.

The structural unit represented by Structural Formula 5 may contain 1 or more photo crosslinkable functional groups; for example, at least $R_3$ may represent the above photo crosslinkable functional group.

The structural unit represented by Structural Formula 5 may contain 1 or more, 2 or more, 3 or more, 4 or more or 5 or more halogen atoms (e.g. a fluorine atom) in addition to the above photo crosslinkable functional group(s). The number of the halogen atoms, such as a fluorine atom, contained in the structural unit may also be 10 or less, 9 or less, 8 or less, 7 or less, or 6 or less.

In the structural unit represented by Structural Formula 5, at least one, 1 to 3 or 1 to 2 among the $R_1$ to $R_5$ may represent the above crosslinkable functional group(s).

In the structural unit represented by Structural Formula 5, 1 or more, 2 or more, 3 or more, 4 or more or 5 or more halogen atoms may be contained in the positions marked as $R_1$ to $R_5$. The number of halogen atoms contained in the positions marked as $R_1$ to $R_5$ may also be 10 or less, 9 or less, 8 or less, 7 or less, or 6 or less.

When the block 2 contains an additional structural unit(s) in addition to the structural unit represented by Structural Formula 5, the proportion of the structural unit represented by Structural Formula 5 may be adjusted to the range in which sufficient crosslinking reactions can take place while the self-assembling property of the block copolymer is maintained. For example, the proportion of the above structural unit (represented by Structural Formula 5) in the block 2 may be about 0.1 mol % to 5 mol %, 0.5 mol % to 5 mol %, 1 mol % to 5 mol %, 1.5 mol % to 5 mol %, 1.5 mol % to 4 mol % or 1.5 mol % to 3 mol % based on the total number of moles of the structural units in the block 2. Such a proportion may be adjusted depending on the types of the structural units or blocks contained in the block copolymer.

The block 2 of a block copolymer may contain another structural unit in addition to the structural unit represented by the above Structural Formula 5. In this case, the type of the structural unit that can be additionally contained is not particularly limited.

For example, the block 2 may additionally contain a polyvinylpyrrolidone structural unit, a polylactic acid structural unit, a poly(vinylpyridine) structural unit, a polystyrene structural unit such as polystyrene and poly(trimethylsilyl styrene), a polyalkylene oxide structural unit such as polyethylene oxide, a polybutadiene structural unit, a polyisoprene structural unit, or a polyolefin structural unit such as polyethylene.

In one embodiment, the block 2 may contain a structural unit that has an aromatic structure with one or more halogen atoms, in addition to the structural unit represented by Structural Formula 5.

For example, the above structural unit may be a structural unit that, unlike Structural Formula 5, does not contain a crosslinkable functional group.

Such a second structural unit of the block 2 may be, for example, a structural unit that is represented by the following Structural Formula 6.

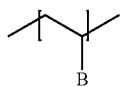

[Structural Formula 6]

In Structural Formula 6, B represents a monovalent substituent having an aromatic structure with one or more halogen atoms.

The block that contains a structural unit such as the above may provide an excellent self-assembling property to the block copolymer to which it belongs, by having an excellent interaction with other blocks such as the block 1.

In Structural Formula 6, the aromatic structure may be, for example, an aromatic structure with 6 to 18 carbons or 6 to 12 carbons.

A fluorine atom or a chlorine atom may be exemplified and a fluorine atom may be preferably selected for the halogen atom(s) of Structural Formula 6, although not limited thereto.

In one embodiment, the B of Structural Formula 6 may be a monovalent substituent having an aromatic structure that contains 6 to 12 carbons and is substituted in part by 1 or more, 2 or more, 3 or more, 4 or more or 5 or more halogen atoms. In the above description, there is no particular limitation to the maximum number of the halogen atoms, and there may be, for example, 10 or less, 9 or less, 8 or less, 7 or less or 6 or less halogen atoms present.

In this case, the above structural unit (represented by Structural Formula 6) may also be represented by the following Structural Formula 7.

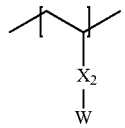

[Structural Formula 7]

In Structural Formula 7, $X_2$ represents a single bond, an oxygen atom, a sulfur atom, —S(=O)$_2$—, an alkylene group, an alkenylene group, an alkynylene group, —C(=O)—$X_1$— or —$X_1$—C(=O)—, where the $X_1$ represents a single bond, an oxygen atom, a sulfur atom, —S(=O)$_2$—, an alkylene group, an alkenylene group or an alkynylene group; and W represents an aryl group with at least one halogen atom. The W may be an aryl group that is substituted in part by at least one halogen atom; for example, it may be an aryl group with 6 to 12 carbons and substituted in part by 2 or more, 3 or more, 4 or more or 5 or more halogen atoms.

In another embodiment, the above structural unit (represented by Structural Formula 6) may also be represented by the following Structural Formula 8.

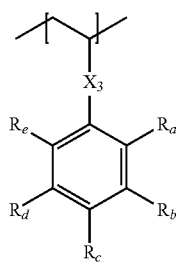

[Structural Formula 8]

In Structural Formula 8, $X_3$ represents a single bond, an oxygen atom, a sulfur atom, —S(=O)$_2$—, an alkylene group, an alkenylene group, an alkynylene group, —C(=O)—$X_1$— or —$X_1$—C(=O)—, where the $X_1$ represents a single bond, an oxygen atom, a sulfur atom, —S(=O)$_2$—, an alkylene group, an alkenylene group or an alkynylene group; and each of $R_a$ to $R_e$ independently represents a hydrogen atom, an alkyl group, a haloalkyl group or a halogen atom, where the number of halogen atoms contained in the positions marked as $R_a$ to $R_e$ is 1 or more.

In another embodiment, the $X_3$ of Structural Formula 8 may represent a single bond, an oxygen atom, an alkylene group, —C(=O)—O—, or —O—C(=O)—.

In Structural Formula 8, each of $R_a$ to $R_e$ independently represents a hydrogen atom, an alkyl group, a haloalkyl group or a halogen atom, and there may be 1 or more, 2 or more, 3 or more, 4 or more or 5 or more halogen atoms (e.g. a fluorine atom) contained in the positions marked as $R_a$ to $R_e$. The number of halogen atoms (e.g. a fluorine atom)

contained in the positions marked as $R_a$ to $R_e$ may also be 10 or less, 9 or less, 8 or less, 7 or less, or 6 or less.

When the block 2 contains the above structural unit that has an aromatic structure with one or more halogen atoms (e.g. a structural unit that is represented by any one of Structural Formulae 6 to 8) in addition to the structural unit represented by Structural Formula 5, the ratio (DH/D5) of the number of moles (DH) of the above structural unit—that has an aromatic structure with one or more halogen atoms— to the number of moles (D5) of the structural unit represented by Structural Formula 5 may be about 35 to 65, about 40 to 60, or about 40 to 50.

The block copolymer of the present application is a block copolymer made up of one or more of each of the aforementioned block 1 and block 2. It may be a diblock copolymer made up only of the above two types of blocks, or it may be a triblock or multiblock (with more than three types of blocks) copolymer which contains 2 or more of either one or both of the block 1 and block 2 or contains another type of block(s) in addition to the block 1 and block 2.

A block copolymer such as the above can inherently exhibit excellent phase separation or an excellent self-assembling property. The phase separation or self-assembling property can be further improved by selecting and combining blocks suitably and satisfying one or more parameters that will be described below in the present specification.

A block copolymer contains 2 or more polymer chains which are connected to one another by a covalent bond(s), and thus phase separation occurs. The block copolymer of the present application exhibits phase separation property and, if needed, can form a nanoscale structure through microphase separation. The form and size of such a nanostructure may be controlled by the size (molecular weight or the like) of the block copolymer or relative ratios among the blocks. Examples of a structure that can be formed through phase separation may include a sphere, a cylinder, a gyroid, a lamella and an inverted structure, and the block copolymer's ability to form such a structure may be referred to as "self-assembling". The inventors recognized—among a variety of block copolymers described above in the present specification—a significant improvement in the self-assembling property, which a block copolymer inherently possesses, in the block copolymers that satisfy at least one among the various parameters that will be described below in the present specification. The block copolymer of the present application may satisfy any one of the parameters, or it may satisfy 2 or more parameters at the same time. Especially, it was recognized that a block copolymer can be made to exhibit vertical orientation by satisfying one or more suitable parameters. In the present application, the term "vertical orientation" refers to the direction in which a block copolymer is oriented and may indicate that the nanostructure formed by the block copolymer is oriented vertically to the direction of a substrate. Technology for controlling the self-assembled structure of a block copolymer either horizontally or vertically on a variety of substrates accounts for a remarkably large part in a practical application of block copolymers. The orientation of a nanostructure in a block copolymer film is generally determined by which block among the blocks constituting the block copolymer is exposed to the surface or in the air. In general, the majority of substrates are polar and the air is nonpolar; therefore, the blocks having higher polarities among the blocks that constitute a block copolymer are seen as wetting a substrate, and the blocks having lower polarities are seen as wetting the interface with the air. Therefore, there are a variety of techniques proposed to enable different types of blocks, each with distinct properties, of a block copolymer wetting at the substrate side simultaneously, the most representative of all is to produce a neutral surface to control the orientation. However, in one aspect of the present application, when the parameters below are properly controlled, a block polymer can be vertically oriented also on a substrate that had not been previously treated by any method, such as surface neutralization, that is well-known in the art to achieve vertical orientation. Also, in another aspect of the present application, vertical orientation as the above can be induced within a short time over a large area through thermal annealing.

The block copolymer of one aspect of the present application can form a film that produces an in-plane diffraction pattern on a hydrophobic surface during grazing-incidence small-angle X-ray scattering (GISAXS). The above block copolymer can form a film that produces an in-plane diffraction pattern on a hydrophilic surface during GISAXS.

In the present application, producing an in-plane diffraction pattern during GISAXS may refer to having peaks that are vertical to the x-component in a GISAXS diffraction pattern during GISAXS analysis. Such peaks are observed due to vertical orientation of a block copolymer. Therefore, a block copolymer producing an in-plane diffraction pattern indicates vertical orientation. In another embodiment, the number of the aforementioned peaks that are observed on the x-component of a GISAXS diffraction pattern may be at least 2, and when multiple peaks are present, the scattering vectors (q values) of the peaks may be identified to have integer ratios, in which case, the phase separation efficiency of the block copolymer can be further improved.

In the present application, errors are accounted for in the term "vertical"; for example, the definition of this term may include an error within the range of ±10 degrees, ±8 degrees, ±6 degrees, ±4 degrees, or ±2 degrees.

The block copolymer capable of forming a film that produces an in-plane diffraction pattern both on a hydrophilic surface and on a hydrophobic surface can exhibit vertical orientation on a variety of surfaces that had not been previously treated by any particular method to induce vertical orientation. In the present application, the term "a hydrophilic surface" refers to a surface whose wetting angle against purified water is in the range of 5 degrees to 20 degrees. Examples of a hydrophilic surface may include, but are not limited to, the surface of silicon that is surface-treated with oxygen plasma, sulfuric acid or a piranha solution. In the present application, the term "a hydrophobic surface" refers to a surface whose room-temperature wetting angle against purified water is in the range of 50 degrees to 70 degrees. Examples of a hydrophobic surface may include, but are not limited to, the surface of polydimethylsiloxane (PDMS) that is surface-treated with oxygen plasma, the surface of silicon that is surface-treated with hexamethyldisilazane (HMDS), and the surface of silicon that is surface-treated with hydrogen fluoride (HF).

Unless specifically indicated otherwise, the properties (e.g. a wetting angle) that may change depending on the temperature in the present application are numerical values that are measured at room temperature. The term "room temperature" refers to the temperature in its natural state, which has not undergone heating or cooling, and may refer to a temperature of about 10° C. to 30° C., about 25° C., or about 23° C.

The film that is formed on a hydrophilic or hydrophobic surface and produces an in-plane diffraction pattern during GISAXS may be a film that has undergone thermal annealing. The film for a GISAXS measurement may be formed, for example, by applying a solution—that is prepared by dissolving the above block copolymer at a concentration of about 0.7 wt % in a solvent (e.g. fluorobenzene)—on the corresponding hydrophilic or hydrophobic surface at a thickness of about 25 nm and a coating area of 2.25 cm² (width: 1.5 cm, length: 1.5 cm) and thermal-annealing the coated layer. The thermal annealing may be carried out, for example, by allowing the above film to be maintained at a temperature of about 160° C. for about 1 hour. GISAXS may be measured by having an X-ray incident on a film, which is prepared in the aforementioned manner, at an angle of incidence in the range of about 0.12 to 0.23 degrees. A diffraction pattern that is scattered from the film can be obtained by a measuring device (e.g. 2D marCCD) that is well-known in the art. The method of using the diffraction pattern to verify the presence or absence of an in-plane diffraction pattern is well-known in the art.

The block copolymer that is observed to have the aforementioned peaks during GISAXS can exhibit an excellent self-assembling property, which can also be controlled effectively depending on the purpose.

The block copolymer of the present application can show at least one peak within a predetermined scattering vector q range during X-ray diffraction (XRD) analysis.

For example, the above block copolymer may have at least one peak in the scattering vector q range of 0.5 $nm^{-1}$ to 10 $nm^{-1}$ during XRD analysis. In another embodiment, the scattering vector q at which the above peak(s) appear(s) may be 0.7 $nm^{-1}$ or more, 0.9 $nm^{-1}$ or more, 1.1 $nm^{-1}$ or more, 1.3 $nm^{-1}$ or more, or 1.5 $nm^{-1}$ or more. Also, in another embodiment, the scattering vector q at which the above peak(s) appear(s) may be 9 $nm^{-1}$ or less, 8 $nm^{-1}$ or less, 7 $nm^{-1}$ or less, 6 $nm^{-1}$ or less, 5 $nm^{-1}$ or less, 4 $nm^{-1}$ or less, 3.5 $nm^{-1}$ or less, or 3 $nm^{-1}$ or less.

The full width at half maximum (FWHM) of the peak(s) that is/are observed within the above scattering vector q range may be in the range of 0.2 to 0.9 $nm^{-1}$. In another embodiment, the above FWHM may be 0.25 $nm^{-1}$ or more, 0.3 $nm^{-1}$ or more, or 0.4 $nm^{-1}$ or more. Also, in another embodiment, the above FWHM may be 0.85 $nm^{-1}$ or less, 0.8 $nm^{-1}$ or less, or 0.75 $nm^{-1}$ or less.

In the present application, the term "full width at half maximum" may refer to the width (i.e. the difference between the two extreme scattering vector q values) of the largest peak at half the maximum amplitude.

The above scattering vector q and FWHM in XRD analysis are numerical values obtained by a numerical analytical method that applies least-squares regression on the XRD analytical result. In the above method, the part that corresponds to the minimum intensity in an XRD diffraction pattern is set as the baseline and the minimum intensity is set as zero, then the peak profile of the above XRD pattern is subject to Gaussian fitting, and the aforementioned scattering vector q and FWHM are obtained from the fitted result. When the above Gaussian fitting is performed, the R-square value is at least 0.9 or more, 0.92 or more, 0.94 or more, or 0.96 or more. The method of obtaining the information from XRD analysis, as mentioned above, is well-known in the art; for example, a numerical analysis program, such as Origin, may be used.

The block copolymer that produces a peak that has the aforementioned FWHM value in the aforementioned scattering vector q range can have a crystalline region that is suitable for self-assembly. The block copolymer that is identified in the aforementioned scattering vector q range can exhibit an excellent self-assembling property.

XRD analysis may be carried out by transmitting X-rays through a block copolymer specimen and then measuring the scattering intensity with respect to a scattering vector. XRD analysis may be carried out on a block copolymer without requiring any particular pretreatment; for example, it may be conducted by drying the block copolymer under a suitable condition and then transmitting X-rays through it. An X-ray whose vertical size is 0.023 mm and horizontal size is 0.3 mm may be used. The scattering vector and FWHM may be obtained through the acquisition of the 2D diffraction pattern—that is scattered from the specimen—in the form of an image by using a measuring device (e.g. 2D marCCD) and the fitting of the acquired diffraction pattern in the aforementioned method.

When at least one of the blocks constituting a block copolymer contains the aforementioned chain as will be described below in the present specification, the number n of the chain-forming atoms in the chain may satisfy both the scattering vector q, which is obtained from the aforementioned XRD analysis, and the following Equation 1.

$$3\ nm^{-1}\ to\ 5\ nm^{-1} = nq/(2\times\pi) \qquad [\text{Equation 1}]$$

In Equation 1, n represents the number of the aforementioned chain-forming atoms, and q represents the smallest scattering vector whose peak is detectable, or the scattering vector that is observed to have the peak with the largest peak area, during the XRD analysis on the above block copolymer. In addition, π represents the ratio of the circumference of a circle to its diameter in Equation 1.

The q and the like of Equation 1 are numerical values that are obtained in the same manner as the description of the aforementioned XRD analysis method.

The q of Equation 1 may be, for example, a scattering vector in the range of 0.5 $nm^{-1}$ to 10 $nm^{-1}$. In another embodiment, the q of Equation 1 may be 0.7 $nm^{-1}$ or more, 0.9 $nm^{-1}$ or more, 1.1 $nm^{-1}$ or more, 1.3 $nm^{-1}$ or more, or 1.5 $nm^{-1}$ or more. Also, in another embodiment, the q of Equation 1 may be 9 $nm^{-1}$ or less, 8 $nm^{-1}$ or less, 7 $nm^{-1}$ or less, 6 $nm^{-1}$ or less, 5 $nm^{-1}$ or less, 4 $nm^{-1}$ or less, 3.5 $nm^{-1}$ or less, or 3 $nm^{-1}$ or less.

Equation 1 describes the relationship between the distance D among the blocks (that contain the aforementioned chain) and the number of chain-forming atoms, when the block copolymer is self-assembled to form a phase-separated structure. When the number of chain-forming atoms in the block copolymer containing the aforementioned chain satisfies Equation 1, the crystallinity of the chain increases, and thereby the phase separation or vertical orientation property can significantly improve. In another embodiment, nq/(2×π) in Equation 1 may be 4.5 $nm^{-1}$ or less. In the above description, the distance (D, in the unit of nm) among the blocks containing the above chain can be calculated by using the equation, D=2×π/q, where D represents the above distance (D, in the unit of nm) among the blocks, and π and q are as defined in Equation 1.

In one aspect of the present application, the absolute value of the difference between the surface energy of the block 1 and the surface energy of the block 2 in a block copolymer may be 10 mN/m or less, 9 mN/m or less, 8 mN/m or less, 7.5 mN/m or less, or 7 mN/m or less. Also, the absolute value of the difference between the above surface energies may be 1.5 mN/m, 2 mN/m, or 2.5 mN/m or more. The structure in which the block 1 and block 2, which have an absolute value of the difference in surface energies in the above range, are connected to each other by covalent bonds can induce microphase separation as the result of phase separation due to a sufficient level of immiscibility. In the above description, the block 1 may be, for example, the aforementioned block that contains the aforementioned chain.

A surface energy may be measured by using the Drop Shape Analyzer DSA100 (manufactured by KRUSS GmbH). Specifically, the surface energy may be measured on the film prepared by applying a coating solution—which is prepared by dissolving the subject specimen to be measured (i.e. a block copolymer or a homopolymer) in fluorobenzene to a solid concentration of about 2 wt %—on a substrate at a thickness of about 50 nm and a coating area of 4 cm$^2$ (width: 2 cm, length: 2 cm), drying at room temperature for about 1 hour, and then thermal-annealing at 160° C. for about 1 hour. The process of measuring a contact angle by dropping deionized water, whose surface tension is well-known in the art, on the above thermal-annealed film is repeated for 5 times, and the 5 measured values of a contact angle are averaged. Similarly, the process of measuring a contact angle by dropping diiodomethane, whose surface tension is well-known in the art, on the above thermal-annealed film is repeated for 5 times, and the 5 measured values of a contact angle are averaged. Subsequently, the surface energies can be obtained by using the averaged values of the contact angle, which were measured respectively with deionized water and diiodomethane, and substituting the numerical value (Strom value) that corresponds to the surface tension of a solvent into the equations according to the Owens-Wendt-Rabel-Kaelble method. The numerical value that corresponds to the surface energy of each block of a block copolymer can be obtained by using the above-described method on a homopolymer that is made up of only the monomer that constitutes the above block.

In the case that the block copolymer contains the aforementioned chain, the block that contains the chain may have a higher surface energy compared to the other block. For example, when the block 1 of a block copolymer contains the above chain, the surface energy of the block 1 may be higher than that of the block 2. In this case, the surface energy of the block 1 may be in the range of about 20 mN/m to 40 mN/m. The surface energy of the above block 1 may be 22 mN/m or more, 24 mN/m or more, 26 mN/m or more, or 28 mN/m or more. Also, the surface energy of the above block 1 may be 38 mN/m or less, 36 mN/m or less, 34 mN/m or less, or 32 mN/m or less. The block copolymer in which the above block 1 is contained and has a surface energy that is different from that of the block 2 as described above can exhibit an excellent self-assembling property.

In a block copolymer, the absolute value of the difference in densities between the block 1 and block 2 may be 0.25 g/cm$^3$ or more, 0.3 g/cm$^3$ or more, 0.35 g/cm$^3$ or more, 0.4 g/cm$^3$ or more, or 0.45 g/cm$^3$ or more. The aforementioned absolute value of the difference in densities may be 0.9 g/cm$^3$ or more, 0.8 g/cm$^3$ or less, 0.7 g/cm$^3$ or less, 0.65 g/cm$^3$ or less, or 0.6 g/cm$^3$ or less. The structure in which the block 1 and block 2 have the absolute value of the difference in densities within the above range and are connected to each other by covalent bonds may induce effective microphase separation as the result of phase separation due to a sufficient level of immiscibility.

The density of each block in the above block copolymer can be measured by using a buoyancy method that is well-known in the art; for example, the density can be measured by analyzing the mass of the block copolymer in a solvent, such as ethanol, whose mass and density in air are known.

When a block copolymer contains the aforementioned chain, the block in which the chain is contained may have a lower density compared to the other block(s). For example, when the block 1 of a block copolymer contains the aforementioned chain, the density of the block 1 may be lower than that of the block 2. In this case, the density of the block 1 may be in the range of about 0.9 g/cm$^3$ to 1.5 g/cm$^3$. The density of the above block 1 may be 0.95 g/cm$^3$ or more. The density of the above block 1 may be 1.4 g/cm$^3$ or less, 1.3 g/cm$^3$ or less, 1.2 g/cm$^3$ or less, 1.1 g/cm$^3$ or less, or 1.05 g/cm$^3$ or less. The block copolymer in which the above block 1 is contained and has a density that is different from that of the block 2 as described above can exhibit an excellent self-assembling property. The aforementioned surface energy and density may be numerical values that are measured at room temperature.

A block copolymer may contain a block whose volume fraction is in the range of 0.4 to 0.8 and a block whose volume fraction is in the range of 0.2 to 0.6. In the case that the block copolymer contains the aforementioned chain, the volume fraction of the block in which the chain is contained may be in the range of 0.4 to 0.8. For example, when the chain is contained in the block 1, the volume fraction of the block 1 may be in the range of 0.4 to 0.8, and the volume fraction of the block 2 may be in the range of 0.2 to 0.6. The sum of volume fractions of the block 1 and block 2 may be equal to 1. The block copolymer that contains each block in the aforementioned volume fraction can exhibit an excellent self-assembling property. The volume fraction of each block in a block copolymer can be obtained based on the density of the block plus the molecular weight, which is measured by gel permeation chromatography (GPC).

The number average molecular weight (Mn) of a block copolymer may be, for example, in the range of 3,000 to 300,000. In the present specification, the term "number average molecular weight" refers to a numerical value that is measured with GPC and calibrated based on a standard polystyrene, and, unless specifically indicated otherwise, the term "molecular weight" in the present specification refers to number average molecular weight. In another embodiment, Mn may be, for example, 3000 or more, 5000 or more, 7000 or more, 9000 or more, 11000 or more, 13000 or more, or 15000 or more. In still another embodiment, Mn may be about 250000 or less, 200000 or less, 180000 or less, 160000 or less, 140000 or less, 120000 or less, 100000 or less, 90000 or less, 80000 or less, 70000 or less, 60000 or less, 50000 or less, 40000 or less, 30000 or less, or 25000 or less. A block copolymer may have a polydispersity (Mw/Mn) in the range of 1.01 to 1.60. In another embodiment, the Mw/Mn may be about 1.1 or more, about 1.2 or more, about 1.3 or more, or about 1.4 or more.

In such a range, a block copolymer can exhibit a sufficient self-assembling property. The Mn and the like of a block copolymer can be adjusted in consideration of the self-assembled structure of interest and the like.

In the case that the block copolymer contains at least the aforementioned block 1 and block 2, the proportion of the block 1 (e.g. the proportion of the block that contains the aforementioned chain) in the above block copolymer may be in the range of 10 mol % to 90 mol %.

In the present application, there is no particular limitation to the detailed method of preparing a block copolymer such as the above, as long as the method includes forming at least one block of the block copolymer by using monomers that can form each of the aforementioned structural unit.

For example, a block copolymer may be prepared in a living radical polymerization (LRP) method that makes use of the above monomers. Examples of the method include synthesis by anionic polymerization in which an organic rare-earth metal complex or organic alkali metal compound is used as the polymerization initiator in the presence of an alkali metal and an inorganic acid salt such as an alkaline earth metal; synthesis by an anionic polymerization method in which an organic alkali metal compound is used as the polymerization initiator in the presence of an organic aluminum compound; an atom transfer radical polymerization (ATRP) method in which an ATRP agent is used as the polymerization-control agent; an activators regenerated by electron transfer (ARGET) ATRP method in which an ATRP agent is used as the polymerization-control agent but the polymerization takes place in the presence of an organic or inorganic reducing agent that generates an electron; an initiators for continuous activator regeneration (ICAR) ATRP method; polymerization by a reversible addition-fragmentation chain transfer (RAFT) method in which an inorganic reducing agent and a RAFT agent are used; and a method of using an organic tellurium compound as the initiator, among which a suitable method may be selected for use.

For example, the aforementioned block copolymer may be prepared through polymerization of a reactant (that includes the monomers capable of forming the aforementioned block) by a living radical polymerization method in the presence of a radical initiator and a living radical polymerization reagent.

There is no particular limitation to the method of forming another block to be contained in a block copolymer together with the block(s) formed of the aforementioned monomers during the preparation of the block copolymer; the monomer(s) may be suitably selected in consideration of the block type of interest for the formation of the other block.

The process of preparing a block copolymer may further include, for example, precipitating, in a nonsolvent, the polymerization product that is produced through the above processes.

There is no particular limitation to the type of the radical initiator, and the radical initiator may be suitably selected in consideration of the polymerization efficiency; for example, an azo compound such as azobisisobutyronitrile (AIBN) and 2,2'-azobis-(2,4-dimethylvaleronitrile), or a peroxide series such as benzoyl peroxide (BPO) and di-t-butyl peroxide (DTBP) may be used.

A living radical polymerization process may be carried out, for example, in a solvent such as methylene chloride, 1,2-dichloroethane, chlorobenzene, dichlorobenzene, benzene, toluene, acetone, chloroform, tetrahydrofuran, dioxane, monoglyme, diglyme, dimethylformamide, dimethyl sulfoxide, and dimethylacetamide.

Examples of a nonsolvent include, but are not limited to, an alcohol (such as methanol, ethanol, n-propanol, and isopropanol), a glycol (such as ethylene glycol), n-hexane, cyclohexane, n-heptane, and an ether (such as petroleum ether).

The present application also relates to a polymer film that contains the aforementioned block copolymer. The polymer film may be used in a variety of applications, for example, in a variety of electronic or electrical devices, in the process of forming the aforementioned patterns, in magnetic storage recording media such as flash memory, or in biosensors.

In one embodiment, the aforementioned block copolymer may realize a regular structure, such as a sphere, a cylinder, a gyroid or a lamella, through self-assembly in the aforementioned polymer film.

For example, the block 1, the block 2 or (in the segment of the other block that is covalently bonded to any of the block 1 and block 2) the segment may form a regular structure such as a lamella form or a cylindrical form in a block copolymer.

The above polymer film in the present application may have an in-plane diffraction pattern, which is a peak(s) vertical to the x-component of a GISAXS diffraction pattern, during GISAXS analysis. In another embodiment, the number of the peaks observed along the x-component of the above GISAXS diffraction pattern may be at least 2 and, when there are multiple peaks present, the scattering vector q values of the peaks may be observed to be in an integer ratio.

The aforementioned block 2 may form a crosslinked structure in a polymer film such as the above. That is, the crosslinked structure may be formed, for example, by a method of crosslinking the crosslinkable functional group of the structural unit of Structural Formula 5 in the above block 2 in the presence of a self-assembled structure. In this case, the condition of forming a crosslinked structure is not particularly limited and may be adjusted in consideration of the type and amount of the crosslinkable functional group used. For example, when the above crosslinkable functional group is one among the aforementioned azide-containing functional group, the crosslinking may be conducted by allowing a self-assembled block copolymer to be maintained at a temperature of about 200° C. to 230° C. for about 30 minutes to 1 hour.

The present application also relates to a method of forming a polymer film by using the aforementioned block copolymer. The method may include forming a polymer film containing the above block copolymer on a substrate in a self-assembled state. For example, the above method may include forming a layer of the above block copolymer or a layer of a coating solution in which the block copolymer is dissolved in a suitable solvent, on a substrate by deposition or the like, and, if needed, it may also include a process of annealing or heat-treating the above layer.

The above annealing or heat-treating (heat-treatment) may be carried out, for example, based on the phase transition temperature or glass transition temperature of the block copolymer; for example, it may be carried out at a temperature equal to or greater than the above glass transition temperature or phase transition temperature. The duration of such a heat-treatment is not particularly limited and may be, for example, in the range of about 1 minute to 72 hours, although it may be subject to change as necessary. Also, the heat-treatment temperature of a polymer thin film may be, for example, about 100° C. to 250° C., which may be subject to change depending on the block copolymer to be used.

In another embodiment, the layer that is formed as the above may be solvent-annealed in a room-temperature non-polar solvent and/or polar solvent for about 1 minute to 72 hours.

The process of crosslinking the above block 2 may be additionally conducted after a polymer film is formed as the above. Such a crosslinking is processed as described above in the present specification.

The present application also relates to a method of forming a pattern. The above method may include, for example, a process of selectively removing the block 1 or block 2 of a block copolymer from the laminate that is made up of a substrate and a polymer film, which is formed on the substrate and contains the above self-assembled block copolymer. The above method may be a method of forming a pattern on the above substrate. For example, the above method may include forming, on a substrate, a polymer film that contains the above block copolymer, selectively removing any one or more blocks of the block copolymer that is present in the above film, and subsequently etching the substrate. The above method enables the formation of a micropattern, for example, in nanoscale. Also, a variety of patterns such as a nanorod and a nanohole may be formed by the above method, depending on the structure of the block copolymer in the polymer film. If needed, the above block copolymer may be mixed with another copolymer, a homopolymer or the like for the formation of patterns. The type of the substrate to be applied in the above method is not particularly limited and may be selected to suit the application; for example, silicon oxide may be used.

The aforementioned block 2 in a polymer film used in the process of selectively removing the above block 1 and/or block 2 may contain a crosslinked structure, where the method of realizing the crosslinked structure is as described above in the present specification.

For example, the above method may form a silicon-oxide nanoscale pattern that exhibits a high aspect ratio. A variety of forms such as a nanorod and a nanohole may be realized, for example, by forming the above polymer film on the silicon oxide, selectively removing any one block of a block copolymer in the above polymer film where the block copolymer constitutes a predetermined structure, and then etching the silicon oxide by any one of various techniques, for example, by reactive-ion etching. Also, the above method may enable the realization of a nanopattern having a high aspect ratio.

For example, the above pattern may be realized in the scale of tens of nanometers, and such a pattern may be used for a variety of applications including, for example, magnetic recording media for the next-generation information and electronics.

For example, a pattern in which nanostructures (e.g. nanowires) whose width is about 3 nm to 40 nm are arranged spaced apart (e.g. by 6 nm to 80 nm) can be formed by the above method. In another embodiment, a structure in which nanoholes whose width (e.g. diameter) is about 3 nm to 40 nm are arranged spaced apart by about 6 nm to 80 nm can also be realized.

In addition, the nanowires or nanoholes in the above structure can be made to have high aspect ratios.

In the above method, there is no particular limitation to the method of selectively removing any one block of a block copolymer; for example, a method of removing a relatively soft block by having the polymer film irradiated with suitable electromagnetic waves such as ultraviolet rays may be used. In this case, the condition of an ultraviolet ray irradiation is determined by the type of blocks in the block copolymer; for example, it may include an irradiation of the ultraviolet rays whose wavelength is about 254 nm for 1 minute to 60 minutes.

In addition, following the ultraviolet ray irradiation, the process of additionally removing the segment that was previously disintegrated by ultraviolet rays may be carried out by treating the polymer film with an acid or the like.

In addition, there is no particular limitation to the process of etching the substrate by using, as the mask, the polymer film that has been selectively removed of certain blocks; for example, the above etching may be carried out through reactive-ion etching with $CF_4$/Ar ions or the like. The above etching may be followed by the process of removing the polymer film from the substrate through an oxygen plasma treatment or the like.

EFFECT

Figure 1:
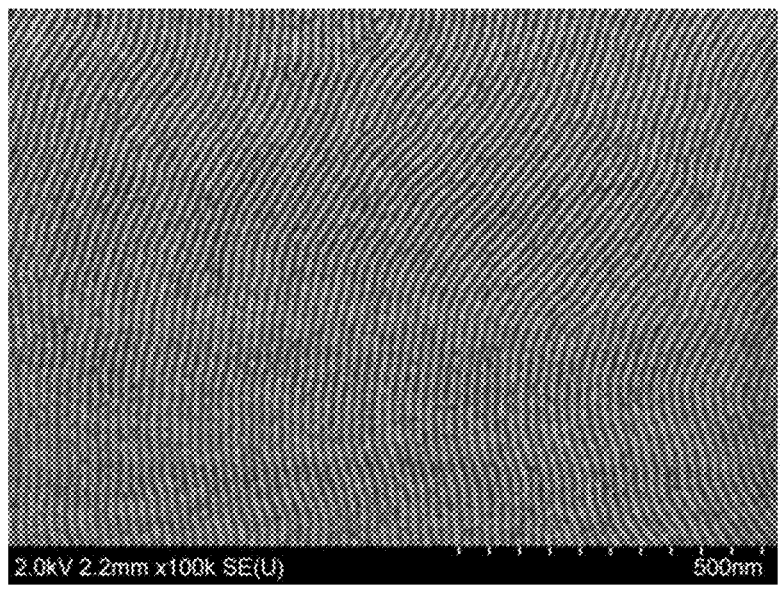
FIG. 1 is a SEM image of a polymer layer that is formed by using a block copolymer of Example 1 and that is before a photo crosslinking.

The present application can provide a block copolymer and uses thereof. The block copolymer of the present application exhibits an excellent self-assembling property or phase separation property, can be provided with a variety of required functions without constraint and, especially, etching selectivity can be secured, making the block copolymer effectively applicable to such uses as pattern formation.

DETAILED DESCRIPTION OF EMBODIMENTS

The present application is described in more detail hereinafter through examples according to the present application, but the scope of the present application is not limited to the examples which are proposed hereinafter.

1. NMR Measurement

NMR analysis was carried out at room temperature by using a NMR spectrometer that includes a Varian Unity Inova (500 MHz) spectrometer with a 5-mm triple resonance probe. The analysis subject material was diluted with a solvent ($CDCl_3$) for an NMR measurement to a concentration of about 10 mg/ml for use, and the chemical shift was expressed in ppm.

<Applied Abbreviations> br=broad signal, s=singlet, d=doublet, dd=doublet of doublets, t=triplet, dt=doublet of triplets, q=quartet, p=quintet, m=multiplet.

2. Gel Permeation Chromatography (GPC)

The number average molecular weight (Mn) and molecular weight distribution were measured by GPC. The analysis subject material such as a macroinitiator or the block copolymer of the examples was put in a 5-mL vial and diluted with tetrahydrofuran (THF) to a concentration of about 1 mg/mL. Then, a standard specimen for calibration and the specimen to be analyzed were filtered with a syringe filter (pore size: 0.45 μm) and subsequently analyzed. ChemStation (Agilent Technologies Inc.) was used as the analytical program, each of the weight average molecular weight (Mw) and Mn was obtained by comparing the elution time of the specimen with the calibration curve, and then a molecular weight distribution (polydispersity index, PDI) was calculated as a ratio (Mw/Mn). The measuring condition of GPC is as follows:

<GPC Measuring Conditions>

Device: 1200 Series of Agilent Technologies Inc.
Column: Two PLgel MIXED-B of Polymer Laboratories
Solvent: THF
Column temperature: 35° C.
Sample concentration: 1 mg/mL, 200 L is injected
Standard specimen: polystyrene (Mp: 3900000, 723000, 316500, 52200, 31400, 7200, 3940, 485)

Preparation Example 1

The compound (DPM-C12) represented by the following Structural Formula A was synthesized by the following method: hydroquinone (10.0 g, 94.2 mmol) and 1-bromododecane (23.5 g, 94.2 mmol) were introduced into a 250-mL flask, dissolved in 100 mL of acetonitrile; then, an excessive amount of potassium carbonate was added to the above solution and allowed to react at about 75° C. for about 48 hours under a nitrogen atmosphere; upon completion of the reaction, the reaction products were removed of the remaining potassium carbonate and of acetonitrile that was used for the reaction; then the substances were worked up through an addition of a mixed solvent of dichloromethane (DCM) and water, and the separated organic layer was dehydrated with $MgSO_4$; subsequently, the substances were purified by column chromatography (CC) with DCM to obtain a white solid intermediate with a yield of about 37%.

<NMR Analysis Results of Intermediate>
$^1$H-NMR (CDCl$_3$): δ6.77 (dd, 4H); δ4.45 (s, 1H); δ3.89 (t, 2H); δ1.75 (p, 2H); δ1.43 (p, 2H); δ1.33-1.26 (m, 16H); δ0.88 (t, 3H).

The synthesized intermediate (9.8 g, 35.2 mmol), methacrylic acid (6.0 g, 69.7 mmol), dicyclohexylcarbodiimide (DCC) (10.8 g, 52.3 mmol) and p-dimethylaminopyridine (DMAP) (1.7 g, 13.9 mmol) were introduced into a flask, 120 mL of methylene chloride was added, and then allowed to react at room temperature for 24 hours under a nitrogen atmosphere; upon completion of the reaction, the reaction products were filtered to be removed of a urea salt that was produced during the reaction and also of the remaining methylene chloride; then, the substances were removed of impurities by column chromatography (CC) that uses hexane and dichloromethane (DCM) as the mobile phase, the obtained products were recrystallized in a mixed solvent of methanol and water (mixed at a weight ratio of 1:1) to obtain a white solid target material (DPM-C12) (7.7 g, 22.2 mmol) with a yield of 63%.

<NMR Analysis Results of DPM-C12>
$^1$H-NMR (CDCl$_3$): δ7.02 (dd, 2H); δ6.89 (dd, 2H); δ6.32 (dt, 1H); δ5.73 (dt, 1H); δ3.94 (t, 2H); δ2.05 (dd, 3H); δ1.76 (p, 2H); δ1.43 (p, 2H); 1.34-1.27 (m, 16H); δ0.88 (t, 3H).

[Structural Formula A]

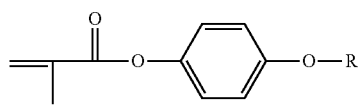

In Structural Formula A, R represents a linear-chain alkyl group with 12 carbons.

Preparation Example 2

3-hydroxy-1,2,4,5-tetrafluorostyrene was synthesized by the following method. Pentafluorostyrene (25 g, 129 mmol) was added to a mixed solution of 400 mL of tert-butanol and potassium hydroxide (37.5 g, 161 mmol) and then reacted for 2 hours (reflux reaction). After cooling the reacted product to room temperature, 1200 mL of water was added thereto and remained butanol used for the reaction was eliminated via volatilization. The reacted product was extracted 3 times by diethyl ether (300 mL); the target materials were precipitated by acidifying the aqueous solution layer with a 10-weight % hydrochloric acid solution to a pH of about 3; and then the organic layer was collected by extracting 3 times by diethyl ether (300 mL).

The organic layer was then dehydrated with $MgSO_4$ and solvent was removed so as to obtain crude product. The crude product was purified by column chromatography by using hexane and dichloromethane (DCM) as the mobile phase to acquire colorless liquid 3-hydroxy-1,2,4,5-tetrafluorostyrene (11.4 g). The results of NMR analysis on the above substance are as follows.

<NMR Analysis Results>
$^1$H-NMR (DMSO-d): δ11.7 (s, 1H); δ6.60 (dd, 1H); δ5.89 (d, 1H); δ5.62 (d, 1H)

The compound of the chemical formula B below was synthesized by the following method. The obtained intermediate (3-hydroxy-1,2,4,5-tetrafluorostyrene) (1.7 g, 7.8 mmol), 4-benzoylbenzoic acid (1.9 g, 8.6 mmol), DCC (dicyclohexylcarbodiimide) (1.8 g, 8.6 mmol) and DMPA (p-dimethylaminopyridine) (0.48 g, 3.1 mmol) were mixed and 30 mL of methylene chloride was added thereto and then the mixture was reacted under nitrogen at room temperature for 24 hours. After the termination of the reaction, urea salt produced during the reaction and remained methylene chloride were eliminated. Impurities were eliminated in a column chromatography using hexane and DCM (dichloromethane) as a mobile phase and then the obtained product was recrystallized in mixed solvent of methanol and water (methanol:water=3:1 (weight ratio)) so as to obtain white solid target material that was the monomer of the chemical formula B with a yield of 70 weight %.

The results of NMR analysis on the above compound is as follows.

<NMR Analysis Results>
$^1$H-NMR (CDCl$_3$): δ8.3 (t, 2H); δ7.9 (q, 2H); δ7.8 (d, 2H); δ7.6 (t, 2H); δ7.5 (dd, 2H); δ6.60 (dd, 1H); δ5.89 (d, 1H); δ5.62 (d, 1H);

[Structural Formula B]

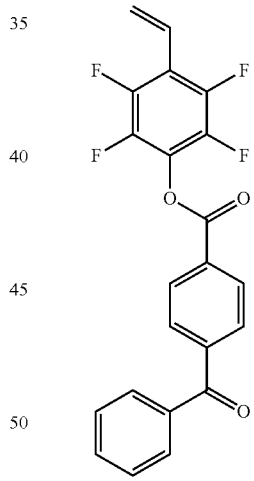

Example 1

2.0 g of the compound (DPM-C12) of Preparation Example 1, 64 mg of a reversible addition-fragmentation chain transfer (RAFT) reagent (2-cyano-2-propyl dodecyl trihiobenzoate), 23 mg of AIBN (azobisisobutyronitrile) and 5.34 mL of anisole were put into a 10 mL Schlenk flask, and stirred at room temperature for 30 minutes under a nitrogen atmosphere to allow an RAFT polymerization reaction at 70° C. for 4 hours. After the polymerization, a reaction solution was precipitated in 250 ml of methanol as an extraction solvent, and dried through decreased pressure filtration, thereby preparing a primrose macroinitiator. The yield of the macroinitiator was about 80 weight %, and the number average molecular weight (Mn) and distribution of molecular weight (Mw/Mn) of the macroinitiator were 6100 and 1.25, respectively.

0.2 g of the obtained macroinitiator, 3.589 g of pentafluorostyrene and 0.151 g of the photo crosslinkable monomer of the structural formula B of Preparation Example 2 and 1.697 mL of anisole were put into a 10 mL Schlenk flask, and stirred at room temperature for 30 minutes under a nitrogen atmosphere to allow an RAFT polymerization reaction at 70° C. for 3 hours. After the polymerization, a reaction solution was precipitated in 250 ml of methanol as an extraction solvent, and dried through decreased pressure filtration, thereby preparing a light yellow block copolymer. The yield of the block copolymer was about 14 weight %, and the number average molecular weight (Mn) and distribution of molecular weight (Mw/Mn) of the block copolymer were 14,400 and 1.21, respectively. The block copolymer includes a first block derived from the compound (DPM-C12) of Preparation Example 1 and a second block derived from the pentafluorostyrene and the compound of the structural formula B in Preparation Example 2.

Test Example 1

Figure 2:
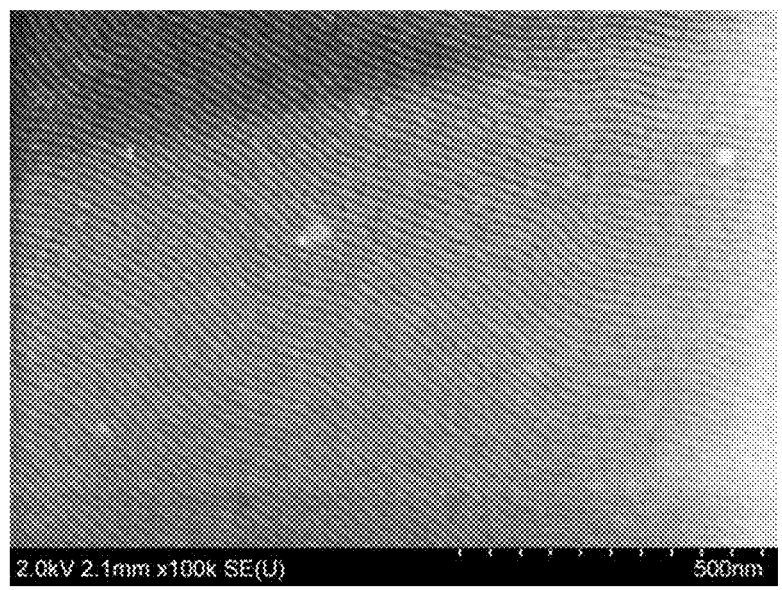
FIG. 2 is a SEM image of a polymer layer that is formed by using a block copolymer of Example 1 and that is after a photo crosslinking.

A self-assembled polymer film was formed by using the block copolymer that was synthesized in Example 1, and the results were observed. The prepared block copolymer was dissolved in a solvent to a concentration of 1.0 weight %; then spin-coated on a silicon wafer for about 60 seconds at a speed of about 3000 rpm and then was subjected to a thermal annealing so as to form a polymer thin film including self assembled block copolymer. FIG. 1 is a SEM image of the obtained polymer thin film. Then the polymer thin film was irradiated with ultraviolet ray. The ultraviolet ray having a wavelength of about 254 nm was irradiated with light intensity of about 2 J/cm². FIG. 2 is a SEM image of the polymer thin film after the above photocrosslinking. As a result of performing solvent washing to the polymer thin film, it was confirmed that the selective etching can be performed.

Figure 3:
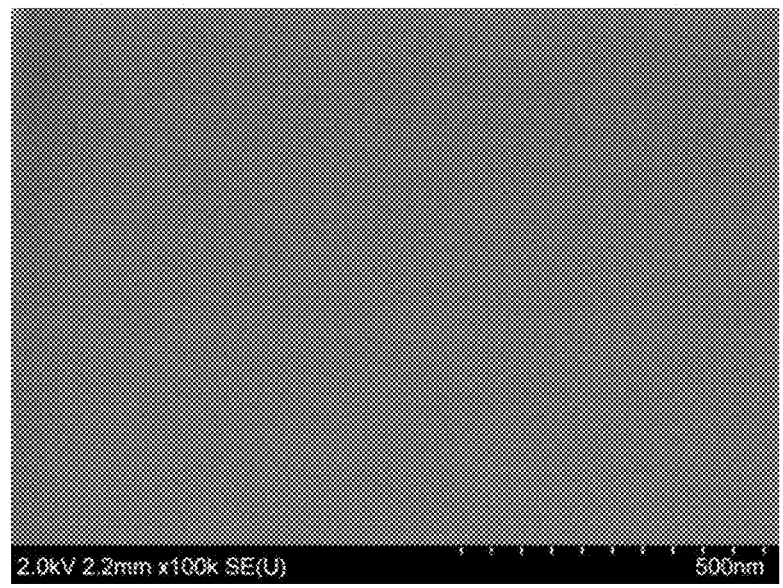
FIG. 3 shows a result after subjecting a polymer layer formed by using a block copolymer of Example 1 to a solvent washing without a photo crosslinking.

FIG. 3 shows the result after performing the solvent washing with respect to a polymer thin film before photo crosslinking process and it can be confirmed from FIG. 3 that the etching selectivity between blocks cannot be obtained.

What is claimed is:

1. A block copolymer comprising a first block comprising a unit represented by Structural Formula 1 below and a second block comprising a unit represented by Structural Formula 3 below:

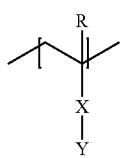

[Structural Formula 1]

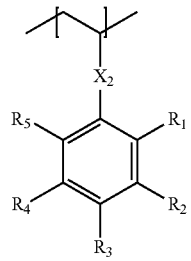

[Structural Formula 3]

wherein, R of the Formula 1 represents a hydrogen atom or an alkyl group; X of the Formula 1 represents a single bond, an oxygen atom, a sulfur atom, —S(=O)$_2$—, a carbonyl group, an alkylene group, an alkenylene group, an alkynylene group, —C(=O)—X$_1$— or —X$_1$—C(=O)—, wherein the X$_1$ represents an oxygen atom, a sulfur atom, —S(=O)$_2$—, an alkylene group, an alkenylene group or an alkynylene group; Y of the Formula 1 represents a monovalent substituent that includes a ring structure to which a linear chain including 8 or more chain-forming atoms is connected; and X$_2$ of the Formula 3 represents a single bond, an oxygen atom, a sulfur atom, —S(=O)$_2$—, an alkylene group, an alkenylene group, an alkynylene group, —C(=O)—X$_2$— or —X$_2$—C(=O)—, wherein the X$_2$ represents a single bond, an oxygen atom, a sulfur atom, —S(=O)$_2$—, an alkylene group, an alkenylene group or an alkynylene group; and each of R$_1$ to R$_5$ of the Formula 3 independently represents a hydrogen atom, an alkyl group, a haloalkyl group, a halogen atom or a photo crosslinkable functional group, wherein one or more of the photo crosslinkable functional groups are included in positions marked as R$_1$ to R$_5$.

2. The block copolymer of claim 1, wherein the X represents a single bond, an oxygen atom, a carbonyl group, —C(=O)—O—, or —O—C(=O)—.

3. The block copolymer of claim 1, wherein the linear chain includes 8 to 20 chain-forming atoms.

4. The block copolymer of claim 1, wherein the chain-forming atom is carbon, oxygen, nitrogen, or sulfur.

5. The block copolymer of claim 1, wherein the chain-forming atom is carbon or oxygen.

6. The block copolymer of claim 1, wherein the ring structure of the Y is an aromatic ring structure or an alicyclic ring structure.

7. The block copolymer of claim 1, wherein the Y of the Structural Formula 1 is represented by Structural Formula 2 below:

 [Structural Formula 2]

where in the Structural Formula 2, P represents an arylene group;

Q represents a single bond, an oxygen atom or —NR$_3$—, wherein the R$_3$ represents a hydrogen atom, an alkyl group, an alkenyl group, an alkynyl group, an alkoxy group or an aryl group; and Z represents a linear chain with 8 or more chain-forming atoms.

8. The block copolymer of claim 1, wherein the photo crosslinkable functional group is benzoylphenoxy group, alkenyloxycarbonyl group, (meth)acryloyl group or alkenyloxyalkyl group.

9. The block copolymer of claim 1, wherein one or more halogen atoms are included in the positions marked as R$_1$ to R$_5$ of the Structural Formula 3.

10. The block copolymer of claim 1, wherein a ratio of the unit represented by the structural formula 3 in the second block is from 0.1 mol % to 5 mol %.

11. The block copolymer of claim 1, wherein the second block further includes a structural unit represented by Structural Formula 4 below:

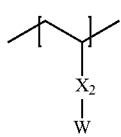

[Structural Formula 4]

where in the Structural Formula 4, $X_2$ represents a single bond, an oxygen atom, a sulfur atom, —S(=O)$_2$—, an alkylene group, an alkenylene group, an alkynylene group, —C(=O)—$X_1$— or —$X_1$—C(=O)—, wherein the $X_1$ represents a single bond, an oxygen atom, a sulfur atom, —S(=O)$_2$—, an alkylene group, an alkenylene group or an alkynylene group; and W represents an aryl group that includes at least one halogen atom.

12. The block copolymer of claim 1, wherein the second block further includes a structural unit represented by Structural Formula 5 below:

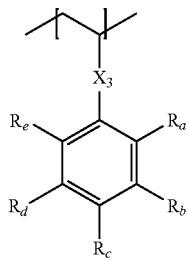

[Structural Formula 5]

where in the Structural Formula 5, $X_3$ represents a single bond, an oxygen atom, a sulfur atom, —S(=O)$_2$—, an alkylene group, an alkenylene group, an alkynylene group, —C(=O)—$X_1$— or —$X_1$—C(=O)—, wherein the $X_1$ represents a single bond, an oxygen atom, a sulfur atom, —S(=O)$_2$—, an alkylene group, an alkenylene group or an alkynylene group; and each of $R_a$ to $R_e$ independently represents a hydrogen atom, an alkyl group, a haloalkyl group or a halogen atom, wherein one or more halogen atoms are included in positions marked as $R_a$ to $R_e$.

13. The block copolymer of claim 12, wherein 3 or more halogen atoms are included in the positions marked as $R_a$ to $R_e$.

14. The block copolymer of claim 12, wherein 5 or more halogen atoms are included in the positions marked as $R_a$ to $R_e$.

15. The block copolymer of claim 12, wherein the halogen atom is a fluorine atom.

16. A polymer film comprising the block copolymer of claim 1, wherein the block copolymer is self-assembled.

17. The polymer film of claim 16, wherein the second block of the block copolymer includes a crosslinked structure.

18. A method of forming a polymer film, the method comprising:
forming a polymer film that includes the block copolymer of claim 1 on a substrate, wherein the block copolymer is self-assembled.

19. The method of claim 18, further comprising: crosslinking of the second block of the block copolymer, wherein the block copolymer is self-assembled.

20. A method of forming a pattern, the method comprising:
selectively removing any one block of the block copolymer of claim 1 from a laminate that is made up of a substrate and a polymer film, which is formed on the substrate and includes the block copolymer, wherein the block copolymer is self-assembled.

21. The polymer film of claim 20, wherein the second block of the block copolymer includes a crosslinked structure.

* * * * *